United States Patent
Zhu

(10) Patent No.: US 9,540,698 B2
(45) Date of Patent: Jan. 10, 2017

(54) MIR-193A-3P AND ASSOCIATED GENES PREDICT TUMORIGENESIS AND CHEMOTHERAPY OUTCOMES

(71) Applicant: Genedia Biotech Co., Ltd., Kunshan, Jiangsu (CN)

(72) Inventor: Jingde Zhu, Jiangsu (CN)

(73) Assignee: Genedia Biotech Co., Ltd., Kunshan, Jiangsu (CN)

( * ) Notice: Subject to any disclaimer, the term of this patent is extended or adjusted under 35 U.S.C. 154(b) by 0 days.

(21) Appl. No.: 14/807,647

(22) Filed: Jul. 23, 2015

(65) Prior Publication Data

US 2016/0017437 A1 Jan. 21, 2016

Related U.S. Application Data

(63) Continuation of application No. 13/829,903, filed on Mar. 14, 2013, now Pat. No. 9,127,320, which is a continuation of application No. PCT/CN2011/082332, filed on Nov. 17, 2011.

(51) Int. Cl.
*G01N 33/574* (2006.01)
*C12Q 1/68* (2006.01)

(52) U.S. Cl.
CPC ....... *C12Q 1/6886* (2013.01); *G01N 33/57484* (2013.01); *C12Q 2600/106* (2013.01); *C12Q 2600/154* (2013.01); *C12Q 2600/158* (2013.01); *C12Q 2600/178* (2013.01); *G01N 2800/52* (2013.01); *G01N 2800/54* (2013.01)

(58) Field of Classification Search
USPC ........ 435/6.11, 91.1, 375, 455; 514/1, 2, 44, 514/274; 424/9.1; 536/23.1
See application file for complete search history.

(56) References Cited

U.S. PATENT DOCUMENTS

2011/0076768 A1 3/2011 Inazawa et al.

FOREIGN PATENT DOCUMENTS

| CN | 101057144 A | 10/2007 |
|---|---|---|
| CN | 2007/1043174 | 12/2008 |
| CN | 101333558 A | 12/2008 |
| WO | WO 2007/147877 | 12/2007 |
| WO | WO 2010/040083 A2 | 4/2010 |

OTHER PUBLICATIONS

Lee et al., "Impact of E2F-1 Expression on Clinical Outcome of Gastric Adenocarcinoma Patients with Adjuvant Chemoradiation Therapy," Clinical Cancer Research, 14:82-8 (2008).
Wang et al. "Moleclular diagnostic index for hepatocellular carcinoma using real-time fluourescent quantitation RT-PCR: a pilot study," World Chinese Journal of Digestology, ISSN 1009-3079 (Chinese) 17(10): 985-91 (2009).
Iacopetta et al. "A polymorphism in the enhancer region of the thymidylate synthase promoter influences the survival of colorectal cancer patients treated with 5-flurouracil," British Journal of Cancer 856): 827-30 (2001).
PCT/CN2011/082332 International Search Report.
Kozaki et al, Cancer Res., vol. 68, No. 7, pp. 2094-2105 (2008).

*Primary Examiner* — Jane Zara
(74) *Attorney, Agent, or Firm* — Sheppard Mullin Richter & Hampton LLP

(57) ABSTRACT

The disclosure provides a correlation between the expression level of the miR-193a gene, which can be regulated by its methylation status, and both tumorigenesis of and the resistance of a cancer cell to a pyrimidine antimetabolite (5-FU) based chemotherapy. In addition to the methylation status and the expression of miR-193a, its downstream genes, such as E2F1, SRSF2, and apoptotic genes such as caspase 2, are also involved and can serve as useful markers for cancer therapy prognosis and for therapy selection.

8 Claims, 11 Drawing Sheets

US 9,540,698 B2

MIR-193A-3P AND ASSOCIATED GENES PREDICT TUMORIGENESIS AND CHEMOTHERAPY OUTCOMES

CROSS-REFERENCE TO RELATED APPLICATIONS

This application is a continuation of U.S. patent application Ser. No. 13/829,903, filed Mar. 14, 2013, which is the National Phase of International Patent Application No. PCT/CN2011/082332, filed Nov. 17, 2011. The contents of these applications are incorporated herein by reference in their entirety.

FIELD OF THE INVENTION

This invention relates to the field of cancer treatments and companion diagnostics.

BACKGROUND

Cancer is a complex disease with extensive genetic and epigenetic defects, the archive of both of which are rapidly updated by the $2^{nd}$ generation sequencing based genome-wide analyses at the DNA sequence, DNA methylation state, and protein and RNA expression levels. At the epigenetic level, a DNA sequence-independent mechanism that underlies the cross-cell generational transmission of gene expression memory, DNA methylation (addition of a methyl group at the cytosine ring of the 5'-CpG-3' dinucleotides) is the best characterized and regarded as a promising molecular indicator for both diagnosis and/or prognostic of cancer. micro-RNAs (miRs) are small noncoding RNAs that regulate at both stability and translation levels in a sequence-specific manner the expression of protein-coding genes, including those controlling the DNA methylation, DNA methylation at the promoter region of a subset of miR genes negatively correlates with their transcription.

Hepatocellular carcinoma (HCC) is one of the most aggressive and common malignancies, having the second highest cancer mortality rate worldwide. Surgical removal of tumors followed by systemic chemotherapy is a preferred treatment for patients with localized disease. Patients with advanced disease are routinely treated by transarterial chemoembolization and systemic chemotherapy using doxorubicin, cisplatin, interferon, or 5-fluorouracil (5-FU), despite their uncertain clinical benefits. New molecular agents and antibodies targeting the defective signaling pathways have also been attempted for treating HCC, so far with limited success. Therefore, there is a compelling need for a robust diagnostics for early detection and (stratification) staging of the disease to maximize clinical benefits and minimize toxicity and cost of nonsurgical treatments.

SUMMARY

The disclosure provides compositions and methods for identifying a cancer patient suitable for a therapy that includes administration of 5-fluorouracil (5-FU) or the like. After determining if a patient is sensitive to the treatment and therefore likely to be successfully treated, the disclosure also provides methods for treating the patients.

The present inventors identified two cancer cell lines (QGY-7703 and HepG2) that are hundreds of times more sensitive to a 5-FU, than other cell lines (SMMC-7721, PLC, BEL-7402, Hep3B, YY-8103 and FOCUS). Genomic profiling at both DNA methylation and miR expression levels was carried out to look for DNA methylation regulated miRs involved in regulating a cancer cell's sensitivity (or resistance) 5-FU.

It has herein discovered that, the expression of miR-193a-3p was greatly repressed, mediated by DNA methylation, in 5-FU sensitive cell lines. At the presence of miR-193a-3p, miR-193a-3p inhibits the expression of E2F1 and SRSF2. Part of SRSF2' activity, which can be activated by DNA damage such as those induced by 5-FU treatment, is to tilt the balance between two splicing forms, the proapoptotic form (e.g., the L-form for caspase 2) and the antiapoptotic form (e.g., the S-form for caspase 2), of apoptotic genes, towards the proapoptotic form. Therefore, methylation of the miR-193a gene decreases the expression of miR-193a-3p and thus increases the expression of E2F1 and SRSF2. The expression of SRSF2, in turn, increases the proapoptotic/antiapoptotic ratio of the apoptotic genes, sensitize the cancer cell to the 5-FU treatment. It is noted that transcription of SRSF2 is also under the regulation of E2F1.

The relationship between the activity of the miR-193a-3p/E2F1/SRSF2/caspase pathway in a cell and the cell's sensitivity to the FU treatment has further been confirmed mechanistically: (1) transfection with a miR-193a-3p antagomir into 5-FU resistant/miR-193a-3p high-expressing HCC cell line (SMMC-7721) increased E2F1 and SRSF2 expression and the cells' sensitivity to 5-FU, by virtue of its repression of the miR-193a-3p level; (2) transfection with miR-193a-3p mimic into 5-FU sensitive/miR-193a-3p low-expressing HCC cell line (QGY-7703) decreased E2F1 and SRSF2 expression and the cells' sensitivity to 5-FU, by virtue of its elevation of miR-193a-3p level; (3) siRNA-medicated repression of SRSF2 essentially phenocopies all the mimic transfection mediated changes in QGY-7703, including increased cancer cells' resistance to 5-FU; and (4) prior to the 5-FU treatment, 5-FU sensitive cells had higher expression increase than the resistant cells, of the L-form of caspase 2 than of the S-form. 5-FU triggered enlargement of the ratio of L-form/S-form was more drastic in 5-FU sensitive than 5-FU resistant cancer cells.

The key observations detailed in liver cancer cells have also been made in breast cancer cells. It is contemplated that other cancers, in particular those that can be treated by 5-FU (e.g., gastric and colon-rectal cancer), have the same 5-FU resistance mechanisms. In addition to chemoresistance, the data also indicate that the miR-193a-3p/E2F1/SRSF2/caspase pathway is involved in tumorigenesis which reflects the clinical behavior of timorous lesion: initiation, progression and recurrence.

The present disclosure therefore demonstrates that genes in the miR-193a-3p/E2F1/SRSF2/caspase pathway are useful markers to predict a cancer cell's sensitivity to 5-FU treatments, as well as a cancer patient's likelihood of tumor recurrence. When a prediction is made, appropriate therapy can be designed. For instance, cancer patients that are predicted to be sensitive to 5-FU treatments can receive the therapy at a relatively conservative manner. Those predicted to be resistant to 5-FU treatments, on the other hand, can receive more progressive treatment, such as a 5-FU along with various gene therapeutic approaches targeting the molecular events specifically for the alterations of the miR-193a-3p/E2F1/SRSF2/caspase pathway to the patient's advantages.

As readily appreciated by the skilled artisan, the observations made in the present disclosure are readily applicable to drugs similar to 5-FU, such as other pyrimidine antimetabolites. Accordingly, any disclosure, including claims, relating to 5-FU in the present application is also broadly applicable to any pyrimidine antimetabolite.

Patients who can benefit from compositions or methods of the present disclosure include, without limitation, those suffering from liver cancer, rectal cancer, colon cancer, colorectal cancer, non-small cell lung cancer, esophageal cancer, breast cancer, renal cancer, glioblastoma, ovarian cancer, prostate cancer, pancreatic cancer. In one aspect, the patient suffers from a gastrointestinal cancer. In another aspect, the patient suffers from a cancer that can be treated by 5-FU, such as liver cancer including hepatocellular cancer, gastric cancer, colorectal cancer and breast cancer. In another aspect, the cancer is either metastatic or non-metastatic, or is a Stage I, II, III, or IV cancer.

DETAILED DESCRIPTION OF THE DISCLOSURE

Figure 1:
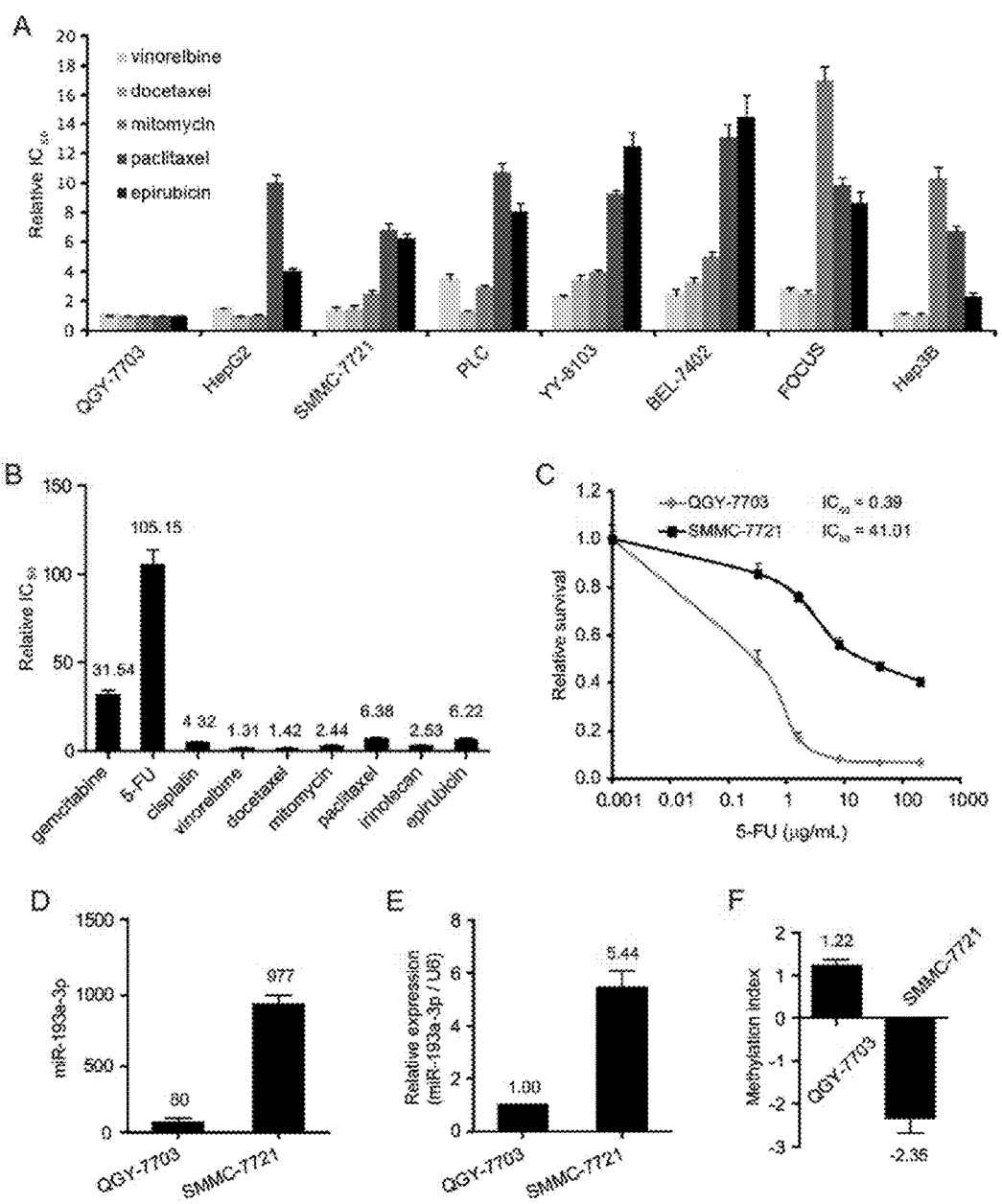
FIG. 1 shows that DNA methylation-regulated miR-193a-3p expression correlated with 5-FU sensitivity as shown between SMMC-7721 and QGY-7703. A. Relative $IC_{50}$ values to each of five chemotherapeutics in each of the other seven HCC cell lines over QGY-7703 were plotted (unit: fold). B. Relative $IC_{50}$ values to each of nine drugs of SMMC-7721 over QGY-7703 were plotted. C. $IC_{50}$ to 5-FU of SMMC-7721 and QGY-7703. The percentage of the relative MTT reads over the each 5-FU dose point was calculated and plotted against $\log_{10}$ μg/mL of 5-FU. D. miR-193a-3p expression was determined by miRomic profiling by using the Solexa sequencing platform (unit: read). E. miR-193a-3p expression was determined by qRT-PCR analysis, digitalized with U6 RNA (arbitrarily as 1). F. DNA methylation state of miR-193a gene was determined by an assay combining the MBD enrichment of heavily methylated DNA fraction and a CpG island array-based analysis. The methylation index: >1=hypermethylated and <0=unmethylated state.

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

The practice of the present disclosure employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook and Russell eds. MOLECULAR CLONING: A LABORATORY MANUAL, $3^{rd}$ edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney $5^{th}$ edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)).

DEFINITIONS

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "patient" intends an animal, a mammal or yet further a human patient. For the purpose of illustration only, a patient includes but is not limited to a human, a simian, a murine, a bovine, an equine, a porcine, a feline, a canine, or an ovine.

The disclosure further provides diagnostic, prognostic and therapeutic methods, which are based, at least in part, on determination of the methylation status and/or expression level of a gene of interest identified herein.

For example, information obtained using the diagnostic assays described herein is useful for determining if a subject is suitable for cancer treatment of a given type (e.g., pyrimidine antimetabolite). Based on the prognostic information, a doctor can recommend a therapeutic protocol, useful for reducing the malignant mass or tumor in the patient or treat cancer in the individual.

Determining whether a subject is suitable or not suitable for cancer treatment of a given type, alternatively, can be expressed as identifying a subject suitable for the cancer treatment or identifying a subject not suitable for the cancer treatment of the given type.

It is to be understood that information obtained using the diagnostic assays described herein may be used alone or in combination with other information, such as, but not limited to, genotypes or expression levels of other genes, clinical chemical parameters, histopathological parameters, or age, gender and weight of the subject. When used alone, the information obtained using the diagnostic assays described herein is useful in determining or identifying the clinical outcome of a treatment, selecting a patient for a treatment, or treating a patient, etc.

When used in combination with other information, on the other hand, the information obtained using the diagnostic assays described herein is useful in aiding in the determination or identification of clinical outcome of a treatment, aiding in the selection of a patient for a treatment, or aiding in the treatment of a patient and etc. In a particular aspect, the genotypes or expression levels of one or more genes as disclosed herein are used in a panel of genes, each of which contributes to the final diagnosis, prognosis or treatment.

Diagnostic and Prognosis Methods

As explained above, the present disclosure demonstrates that genes in the miR-193a-3p/E2F1/SRSF2/caspase pathway are useful markers to predict the probability to advance and 5-FU chemoresistance of the cancer. In particular, they are useful to predict an individual's likelihood of a cancer cell's sensitivity to treatments comprising the administration of 5-FU, and a cancer patient's likely tumor recurrence following a therapy.

Genes in the miR-193a-3p/E2F1/SRSF2/caspase pathway, as the present disclosure demonstrates, can include the miR-193a gene (and miR-193a-3p, one of its two mature miRs), the E2F1 (E2F transcription factor 1) gene, the SRSF2 (serine/arginine-rich splicing factor 2) gene, and any apoptotic genes regulated by SRSF2, including without limitation, caspase 2, 8, 9, C-Flip (FADD-like apoptosis regulator), and bcl-x.

"miR-193a" is microRNA gene. A representative sequence can be found at the GenBank with accession number NR_029710 (human). "miR-193a-3p" is a mature microRNA derived from the precursor microRNA miR-193a. A representative sequence of miR-193a-3p can be found at the microRNA database (mirdb.org) with Sanger accession No: MIMAT0000459: 5'-aacuggccuacaaaguc-ccagu-3' (human, length=22).

It is discovered that the expression of miR-193a-3p is regulated by the methylation status of the miR-193a gene. DNA methylation occurs at the CpG dinucleotides, in particular at those so called "CpG island" near a gene's promoter sequence. Detection of DNA methylation can be carried out by methods such as methylation-specific PCR (MSP), bisulfate sequencing (BSP) and DNA methylation sensitive digestion based methods. CpG sites involved in the regulation of miR-193a-3p expression have been identified and commercial kits are available to carry out the detection of the methylation of these sites. For instance, Table 1 lists MSP and BSP primers for the detection of miR-193a gene methylation.

As used herein, the term "E2F1", or "E2F transcription factor 1" refers to a protein having an amino acid sequence substantially identical to any of the representative E2F1 sequences of NP_005216.1 (human), NP_031917.1 (mouse), or NP_001094248.1 (rat). Suitable cDNA encoding E2F1 is provided at GenBank Accession Nos. NM_005225.2 (human), NM_007891.4 (mouse) or NM_001100778.1 (rat). In one aspect, E2F1 is a gene of the E2F family of transcription factors. The E2F family plays a role in the control of cell cycle and action of tumor suppressor proteins and is also a target of the transforming proteins of small DNA tumor viruses.

As used herein, the term "SRSF2", or "serine/arginine-rich splicing factor 2" refers to a protein having an amino acid sequence substantially identical to any of the representative SRSF2 sequences of NP_001182356.1 (human), NP_035488.1 (mouse), or NP_001009720.1 (rat). Suitable cDNA encoding SRSF2 is provided at GenBank Accession Nos. NM_001195427.1 (human), NM_011358.2 (mouse) or NM_001009720.2 (rat).

As used herein, the term "CASP2", or "caspase 2" refers to a protein having an amino acid sequence substantially identical to any of the representative SRSF2 sequences of NP_116764.2 (human), NP_031636.1 (mouse), or NP_071967.2 (rat). Suitable cDNA encoding E2F1 is provided at GenBank Accession Nos. NM_032982.3 (human), NM_007610.1 (mouse) or NM_022522.2 (rat).

Figure 11:
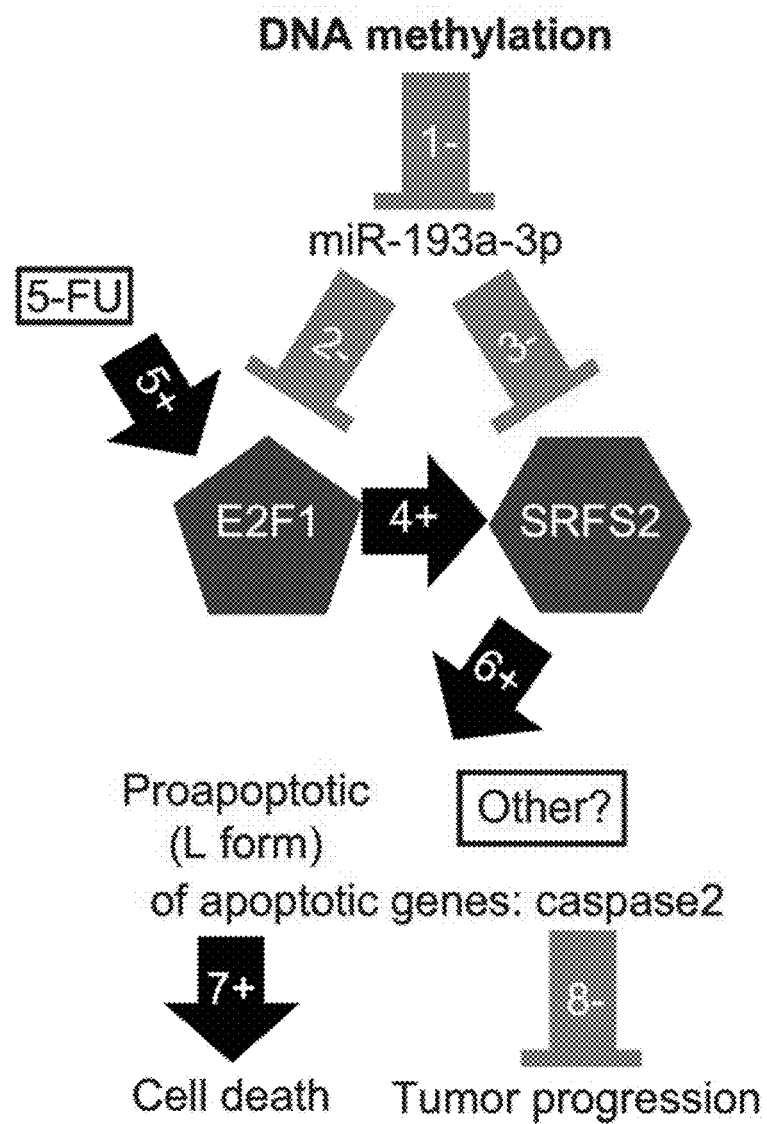
FIG. 11 illustrates a model for mechanism of action. Expression of miR-193a-3p is suppressed by the hypermethylated state of its promoter (1-). miR-193a-3p suppresses both E2F1 and SRSF2 expression at the posttranscriptional levels (2- and 3-). The function of E2F1 is activated by 5-FU treatment (5+), which activates the transcription and therefore activity of SRSF2 (4+). SRSF2 preferentially up-regulates the proapoptotic splicing form (6+) to the antiapoptotic splicing form of caspase 2 (6-) transcripts, potentiating cell death (7+). It is quite possible for the involvement of the other genes under SRSF2 regulation at the alternative mRNA splicing level to be in control of 5-FU chemoresistance and the in vivo tumor growth (8-).

As illustrated in FIG. 11, miR-193a-3p inhibits the expression of E2F1 and SRSF2. Part of SRSF2' activity, which can be activated by DNA damage, is to tilt the balance between two splicing forms, the proapoptotic form (e.g., the L-form for caspase 2) and the antiapoptotic form (e.g., the S-form for caspase 2), of apoptotic genes, towards the proapoptotic form. Therefore, at the presence of miR-193a-3p, the activity of E2F1 and SRSF2 is inhibited and DNA damage does not lead to cell apoptosis, resulting in tumorigenesis and chemoresistance.

On the other hand, methylation of the miR-193a gene decreases the expression of miR-193a-3p and thus increases the expression of E2F1 and SRSF2, leading to increased ratio of proapoptotic/antiapoptotic forms of the apoptotic genes, promoting cancer cell apoptosis, leading to enhanced sensitivity to the 5-FU treatment.

Accordingly, any one or more of the following: (1) methylation of the miR-193a gene, (2) decreased expression of the miR-193a-3p RNA, (3) increased expression of the E2F1 gene, (4) increased expression of the SRSF2 gene, or (5) increased ratio of proapoptotic/antiapoptotic forms of the apoptotic genes regulated by SRSF2 such as caspase 2, 8, 9, C-Flip, bcl-X, is indicative of decreased tumorigenesis and increased sensitivity to a chemotherapy that comprises the administration of 5-FU or a drug alike. Likewise, if the above is not observed or if the opposite of the above is observed, it is indicative of increased tumorigenesis and increased chemoresistance.

Determination of Increase or Decrease of an Expression Level or a Ratio

It would be readily appreciated by the skilled artisan that the increase or decrease of an expression level or a ratio are relative terms but can be readily ascertained.

In one aspect, an "internal control" can be used to normalize the measurement to correct sample collection variations. One such internal control is a "house keeping" gene that refers to any constitutively or globally expressed gene. Examples of such genes include, but are not limited to, β-actin, the transferring receptor gene, GAPDH gene or equivalents thereof. In one aspect of the disclosure, the internal control gene is β-actin. In one of aspect of the disclosure, the internal control gene for the miR-193a-3p is U6 RNA.

Normalized expression levels or ratios can then be compared to a suitable control sample. In one aspect, the control sample is a sample collected from a non-diseased subject or a non-diseased sample from the same subject.

In some such aspects, the term "overexpression" or "underexpression" refers to increased or decreased expression, or alternatively a differential expression, of a gene in a test sample as compared to the expression level of that gene in the control sample. In one aspect, the test sample is a diseased cell, and the control sample is a normal cell. In another aspect, the test sample is an experimentally manipulated or biologically altered cell, and the control sample is the cell prior to the experimental manipulation or biological alteration. In yet another aspect, the test sample is a sample from a patient, and the control sample is a similar sample from a healthy individual. In a yet further aspect, the test sample is a sample from a patient and the control sample is a similar sample from patient not having the desired clinical outcome. In one aspect, the differential expression is about 1.5 times, or alternatively, about 2.0 times, or alternatively, about 2.0 times, or alternatively, about 3.0 times, or alternatively, about 5 times, or alternatively, about 10 times, or alternatively about 50 times, or yet further alternatively more than about 100 times higher or lower than the expression level detected in the control sample. Alternatively, the gene is referred to as "over expressed" or "under expressed". Alternatively, the gene may also be referred to as "up regulated" or "down regulated".

In certain situations, no appropriate control samples can be identified, and the comparison is between two or more states of a sample, none of which is considered as a "norm". For instance, when neither "sensitive" nor "resistant" to a chemotherapy is considered the norm, the comparison can be made between each other or against a value that separates them.

In one scenario, the comparison is made between each other. For instance, it is observed that tumor cells resistant to 5-FU therapy generally have an expression level of Gene A that is about the same as the expression level of a housekeeping gene, GAPDH, and is rarely 2× or more higher than that. Meanwhile, it is observed that tumor cells sensitive to 5-FU typically have much higher expression levels for Gene A. Accordingly, when the expression level of Gene A in a new test sample is measured as 10× as high as the expression level of GAPDH, it can be considered that the expression of Gene A in the new test sample is "increased," which thus indicates that the new test sample is likely sensitive to 5-FU treatment.

In an alternative scenario, the increase or decrease can be compared to a "predetermined value" that separates two different states.

A "predetermined value" for a gene as used herein, is so chosen that a patient with an expression level of that gene higher than the predetermined value is likely to experience a more or less desirable clinical outcome than patients with expression levels of the same gene lower than the predetermined value, or vice-versa. Expression levels of genes, such as those disclosed in the present disclosure, are associated with clinical outcomes. One of skill in the art can determine a predetermined value for a gene by comparing expression levels of a gene in patients with more desirable clinical outcomes to those with less desirable clinical outcomes. In one aspect, a predetermined value is a gene expression value that best separates patients into a group with more desirable clinical outcomes and a group with less desirable clinical outcomes. Such a gene expression value can be mathematically or statistically determined with methods known in the art.

Using the same example as used above, if cells that are resistant to 5-FU treatment generally have an expression level of 1× (times of GADPH expression level) of Gene A, and cells that are sensitive to 5-FU treatment generally have an expression level of 5× (times of GADPH expression level), the predetermined value, for instance, can be set as 3× (times of GADPH expression level). Accordingly, an expression level of 1.5× (times of GADPH expression level) for Gene A in a new test sample would be considered "decreased", or lower than the predetermined value, which then indicates that the new test sample is likely resistant to 5-FU treatment.

Diagnosis and Prognosis

Accordingly, diagnosis or prognosis can be made based on the measured value of the methylation status or activity or expression of the miR-193-3p/E2F1/SRSF2/caspase pathway genes, such as:

(a) the methylation status of one or more CpG sites associated with the miR-193a gene, (b) the expression level of the miR-193a-3p RNA, (c) the mRNA or protein expression level of the E2F1 gene, (d) the mRNA or protein expression level of the SRSF2 gene, or (e) the ratio between the L-form transcript and the S-form transcript of the caspase 2 gene.

Once the measurement is made, prediction can be carried out, in which:

(f) methylation of one or more CpG sites associated with the miR-193a gene, (g) decreased expression level of the miR-193a-3p RNA, (h) increased mRNA or protein expression level of the E2F1 gene, (i) increased mRNA or protein expression level of the SRSF2 gene, or (j) increased ratio between the L-form transcript and the S-form transcript of the caspase 2 gene predicts likely positive clinical outcomes, and the absence thereof predicates likely negative clinical outcomes. In one aspect, the increase or decrease is as compared to a control patient that has the same cancer and is resistant to the therapy. In another aspect, the increase or decrease is as compared to a predetermined value that separates or distinguishes patients that have the same cancer but either are resistant or not resistant to the therapy.

In another aspect, the prediction is made, in which:

(k) no methylation of one or more CpG sites associated with the miR-193a gene, (l) increased expression level of the miR-193a-3p RNA, (m) decreased mRNA or protein expression level of the E2F1 gene, (n) decreased mRNA or protein expression level of the SRSF2 gene, or (o) decreased ratio between the L-form transcript and the S-form transcript of the caspase 2 gene predicts likely negative clinical outcomes, and the absence thereof predicates likely positive clinical outcomes. In one aspect, the increase or decrease is as compared to a control patient that has the same cancer and is not resistant to the therapy. In another aspect, the increase or decrease is as compared to a predetermined value that separates or distinguishes patients that have the same cancer but either are resistant or not resistant to the therapy.

In one aspect, any one or more of (f)-(j) indicates likely positive outcome. In another aspect, any two or more of (f)-(j) indicate likely positive outcome. In another aspect, any three or more of (f)-(j) indicate likely positive outcome. In another aspect, any four or more of (f)-(j) indicate likely positive outcome. In yet another aspect, when all five of (f)-(j) are present, likely positive outcome is indicated.

In another aspect, any one or more of (k)-(o) indicates likely negative outcome. In another aspect, any two or more of (k)-(o) indicate likely negative outcome. In another aspect, any three or more of (k)-(o) indicate likely negative outcome. In another aspect, any four or more of (k)-(o) indicate likely negative outcome. In yet another aspect, when all five of (k)-(o) are present, likely negative outcome is indicated.

Predicable Clinical Outcomes

Clinical outcomes include, without limitation, response to therapy, overall survival or progression free survival, tumor recurrence, and adverse effects. Collectively, when a patient shows one or more positive clinical outcomes, the patient is considered "suitable" for the therapy, and therefore can be "selected" for the therapy.

"Response" to a therapy as used herein, generally refers a change of tumor mass in response to the therapy. More specifically, the terms "complete response," "partial response," "stable disease," "progressive disease," and "no response" are used to describe the level of tumor response.

A "complete response" (CR) to a therapy defines patients with evaluable but non-measurable disease, whose tumor and all evidence of disease had disappeared. A "partial response" (PR) to a therapy defines patients with anything less than complete response that were simply categorized as demonstrating partial response. "Stable disease" (SD) indicates that the patient is stable. "Progressive disease" (PD) indicates that the tumor has grown (i.e. become larger), spread (i.e. metastasized to another tissue or organ) or the overall cancer has gotten worse following treatment. For example, tumor growth of more than 20 percent since the start of treatment typically indicates progressive disease. "Disease free survival" indicates the length of time after treatment of a cancer or tumor during which a patient survives with no signs of the cancer or tumor. "Non-response" (NR) to a therapy defines patients whose tumor or evidence of disease has remained constant or has progressed.

The term "likely to respond" intends to mean that a patient is relatively more likely to experience a complete response or partial response than patients similarly situated without the methylation status or expression. Alternatively, the term "not likely to respond" intends to mean that the patient of a methylation status or expression is relatively less likely to experience a complete response or partial response than patients similarly situated without the genotype.

"Overall Survival" (OS) intends a prolongation in life expectancy as compared to naïve or untreated individuals or patients. Overall survival can be expressed as days, months or years of life span following the therapy.

"Progression free survival" (PFS) indicates the length of time during and after treatment that the cancer does not grow. Progression-free survival includes the amount of time patients have experienced a complete response or a partial response, as well as the amount of time patients have experienced stable disease.

"Tumor Recurrence" as used herein and as defined by the National Cancer Institute is cancer that has recurred (come back), usually after a period of time during which the cancer could not be detected. The cancer may come back to the same place as the original (primary) tumor or to another place in the body. It is also called recurrent cancer.

The term "suitable for a therapy" or "suitably treated with a therapy" shall mean that the patient is likely to exhibit one or more favorable clinical outcome as compared to a patient or patients having the same disease and receiving the same therapy but possessing a different characteristic that is under consideration for the purpose of the comparison. In one aspect, the characteristic under consideration is DNA methylation. In another aspect, the characteristic under consideration is expression level of a gene or a polypeptide. In one aspect, a more desirable clinical outcome is relatively higher likelihood of or relatively better tumor response such as tumor load reduction. In another aspect, a more desirable clinical outcome is relatively longer overall survival. In yet another aspect, a more desirable clinical outcome is relatively longer progression free survival or time to tumor progression. In yet another aspect, a more desirable clinical outcome is relatively longer disease free survival. In further another aspect, a more desirable clinical outcome is relative reduction or delay in tumor recurrence. In another aspect, a more desirable clinical outcome is relatively decreased metastasis. In another aspect, a more desirable clinical outcome is relatively lower relative risk. In yet another aspect, a more desirable clinical outcome is relatively reduced toxicity or side effects. In some embodiments, more than one clinical outcomes are considered simultaneously. In one such aspect, a patient possessing a characteristic may exhibit more than one more desirable clinical outcomes as compared to a patient to patients having the same disease and receiving the same therapy but not possessing the characteristic. As defined herein, the patient is considered suitable for the therapy. In another such aspect, a patient possessing a characteristic may exhibit one or more more desirable clinical outcome but simultaneously exhibit one or more less desirable clinical outcome. The clinical outcomes will then be considered collectively, and a decision as to whether the patient is suitable for the therapy will be made accordingly, taking into account the patient's specific situation and the relevance of the clinical outcomes. In some embodiments, disease free survival, progression free survival or overall survival is weighted more heavily than tumor response in a collective decision making.

Thus, one embodiment of the present disclosure provides a method for aiding in the determination of or for determining whether or not a cancer patient is suitable for a therapy comprising the administration of 5-FU, the method comprising measuring, in a tumor sample isolated from the patient, one or more of:
  (a) the methylation status of one or more CpG sites associated with the miR-193a gene,
  (b) the expression level of the miR-193a-3p RNA,
  (c) the mRNA or protein expression level of the E2F1 gene,
  (d) the mRNA or protein expression level of the SRSF2 gene, or
  (e) the ratio between the L-form transcript and the S-form transcript of the caspase 2 gene, wherein the presence of one or more of:
  (f) methylation of the one or more CpG sites associated with the miR-193a gene,
  (g) decreased expression level of the miR-193a-3p RNA,
  (h) increased mRNA or protein expression level of the E2F1 gene,
  (i) increased mRNA or protein expression level of the SRSF2 gene, or
  (j) increased ratio between the L-form transcript and the S-form transcript of the caspase 2 gene determines that the patient is suitable for the therapy, or the presence of none of (f) to (j) determines that the patient is not suitable for the therapy, wherein the increase or decrease is as compared to a control patient that has the same cancer and is resistant to the therapy.

Another embodiment provides a method for aiding in the selection of or for selecting or not selecting a cancer patient for a therapy comprising the administration of 5-FU, the method comprising measuring, in a tumor sample isolated from the patient, one or more of:
  (a) the methylation status of one or more CpG sites associated with the miR-193a gene,
  (b) the expression level of the miR-193a-3p RNA,
  (c) the mRNA or protein expression level of the E2F1 gene,
  (d) the mRNA or protein expression level of the SRSF2 gene, or
  (e) the ratio between the L-form transcript and the S-form transcript of the caspase 2 gene, wherein the patient is selected for the therapy if one or more of:
  (f) methylation of the one or more CpG sites associated with the miR-193a gene,
  (g) decreased expression level of the miR-193a-3p RNA,
  (h) increased mRNA or protein expression level of the E2F1 gene,
  (i) increased mRNA or protein expression level of the SRSF2 gene, or
  (j) increased ratio between the L-form transcript and the S-form transcript of the caspase 2 gene is present, or the patient is not selected for the therapy if none of (f) to (j) is present, wherein the increase or decrease is as compared to a control patient that has the same cancer and is resistant to the therapy.

Yet another embodiment of the disclosure provides a method for aiding in the determination of or for determining whether or not a cancer patient is likely to respond to a therapy comprising the administration of 5-FU, the method comprising measuring, in a tumor sample isolated from the patient, one or more of:
  (a) the methylation status of one or more CpG sites associated with the miR-193a gene,
  (b) the expression level of the miR-193a-3p RNA,
  (c) the mRNA or protein expression level of the E2F1 gene,
  (d) the mRNA or protein expression level of the SRSF2 gene, or
  (e) the ratio between the L-form transcript and the S-form transcript of the caspase 2 gene, wherein the presence of one or more of:
  (f) methylation of one or more CpG sites associated with the miR-193a gene,
  (g) decreased expression level of the miR-193a-3p RNA,
  (h) increased mRNA or protein expression level of the E2F1 gene,
  (i) increased mRNA or protein expression level of the SRSF2 gene, or
  (j) increased ratio between the L-form transcript and the S-form transcript of the caspase 2 gene determines that the patient is likely to respond to the therapy, or the presence of none of (f) to (j) determines that the patient is not likely respond to the therapy, wherein the increase or decrease is as compared to a control patient that has the same cancer and is resistant to the therapy.

Still in another embodiment, the present disclosure provides a method for aiding in the determination of or for determining whether or not a cancer patient is likely to be resistant to a therapy comprising the administration of 5-FU, the method comprising measuring, in a tumor sample isolated from the patient, one or more of:
  (a) the methylation status of one or more CpG sites associated with the miR-193a gene,
  (b) the expression level of the miR-193a-3p RNA,
  (c) the mRNA or protein expression level of the E2F1 gene,
  (d) the mRNA or protein expression level of the SRSF2 gene, or
  (e) the ratio between the L-form transcript and the S-form transcript of the caspase 2 gene, wherein the presence of one or more of:
  (f) methylation of the one or more CpG sites associated with the miR-193a gene,
  (g) decreased expression level of the miR-193a-3p RNA,
  (h) increased mRNA or protein expression level of the E2F1 gene,
  (i) increased mRNA or protein expression level of the SRSF2 gene, or
  (j) increased ratio between the L-form transcript and the S-form transcript of the caspase 2 gene determines that the patient is not likely to be resistant to the therapy, or the presence of none of (f) to (j) determines that the patient is likely to be resistant to the therapy, wherein the increase or decrease is as compared to a control patient that has the same cancer and is resistant to the therapy.

Still, one embodiment provides a method for aiding in the determination of or for determining whether or not a cancer patient is likely to develop tumor recurrence following a therapy, the method comprising measuring, in a tumor sample isolated from the patient, one or more of:
  (a) the methylation status of one or more CpG sites associated with the miR-193a gene,
  (b) the expression level of the miR-193a-3p RNA,
  (c) the mRNA or protein expression level of the E2F1 gene,
  (d) the mRNA or protein expression level of the SRSF2 gene, or
  (e) the ratio between the L-form transcript and the S-form transcript of the caspase 2 gene, wherein the presence of one or more of:
  (f) methylation of the one or more CpG sites associated with the miR-193a gene,
  (g) decreased expression level of the miR-193a-3p RNA, (h) increased mRNA or protein expression level of the E2F1 gene, (i) increased mRNA or protein expression level of the SRSF2 gene, or (j) increased ratio between the L-form transcript and the S-form transcript of the caspase 2 gene determines that the patient is not likely to develop tumor recurrence, or the presence of none of (f) to (j) determines that the patient is likely to develop tumor recurrence, wherein the increase or decrease is as compared to a control patient that has the same cancer and is resistant to the therapy. In some aspects, the therapy comprises 5-FU, or a pyrimidine antimetabolite.

It is noted that, even though the above embodiments use relative increase or decrease values to predict the clinical outcome, where the increase or decrease is as compared to a control patient that has the same cancer and is resistant to the therapy, the comparison can be alternatively made to appropriate predetermined values, as described above.

Pyrimidine antimetabolite includes, without limitation, fluorouracil (5-FU), its equivalents and prodrugs. In one embodiment, a pyrimidine antimetabolite is a chemical that inhibits the use of a pyrimidine. The presence of antimetabolites can have toxic effects on cells, such as halting cell growth and cell division, so these compounds can be used as chemotherapy for cancer.

Fluorouracil (5-FU) belongs to the family of therapy drugs call pyrimidine based anti-metabolites. It is a pyrimidine analog, which is transformed into different cytotoxic metabolites that are then incorporated into DNA and RNA thereby inducing cell cycle arrest and apoptosis. Chemical equivalents are pyrimidine analogs which result in disruption of DNA replication. Chemical equivalents inhibit cell cycle progression at S phase resulting in the disruption of cell cycle and consequently apoptosis. Equivalents to 5-FU include prodrugs, analogs and derivative thereof such as 5'-deoxy-5-fluorouridine (doxifluoridine), 1-tetrahydrofuranyl-5-fluorouracil (ftorafur), Capecitabine (Xeloda), S-1 (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Capecitabine is a prodrug of 5-FU that is converted to its active form by the tumor-specific enzyme PynPase following a pathway of three enzymatic steps and two intermediary metabolites, 5'-deoxy-5-fluorocytidine (5'-DFCR) and 5'-deoxy-5-fluorouridine (5'-DFUR). Capecitabine is marketed by Roche under the trade name Xeloda®.

In one aspect, the term "equivalent" of "chemical equivalent" of a chemical means the ability of the chemical to selectively interact with its target protein, DNA, RNA or fragment thereof as measured by the inactivation of the target protein, incorporation of the chemical into the DNA or RNA or other suitable methods. Chemical equivalents include, but are not limited to, those agents with the same or similar biological activity and include, without limitation a pharmaceutically acceptable salt or mixtures thereof that interact with and/or inactivate the same target protein, DNA, or RNA as the reference chemical.

A "tumor sample" refers to any biological sample collected from a cancer patient that contains a tumor cell, a tumor DNA or RNA, or tumor protein or the like. It is appreciated that tumor cells can be collected from surgical resection or biopsy. As tumor cells can be leaked into the circulation system in a patient, tumor cells can be collected from blood or other circulation tissues. When a tumor cell breaks down, it can release certain DNA, RNA or protein that is characteristic of the tumor, such as methylated or mutated DNA that does not appear in normal cells. As such, a tumor sample does not necessarily include a tumor cell.

In another aspect, a tumor sample is any biological sample that contains substance or information, such as genetic polymorphisms, useful for revealing the status of a tumor. A "biological sample" as used herein includes, without limitation, a tissue or bodily fluid obtained from an animal, preferably a mammal and most preferably a human. For example, a biological sample can be biopsy material, bone marrow samples, blood, blood plasma, serum or cellular fraction thereof, urine, saliva, tears, or cells derived from a biological source. In one embodiment, the mammal is a human suspected of having or previously diagnosed as having or in need of screening for a cancer.

In some aspects, the tumor sample is collected for the measurement before the therapy is administered to the patient. In another aspect, the tumor sample is collected during the therapy, of after the therapy.

In one aspect, patients who can benefit from compositions or methods of the present disclosure include, without limitation, those suffering from liver cancer, rectal cancer, colon cancer, colorectal cancer, non-small cell lung cancer, esophageal cancer, breast cancer, renal cancer, glioblastoma, ovarian cancer, prostate cancer, pancreatic cancer. In another aspect, the cancer is either metastatic or non-metastatic, or is a Stage I, II, III, or IV cancer.

In one aspect, the cancer patient suffers from a gastrointestinal cancer. "Gastrointestinal cancer" refers to malignant conditions of the gastrointestinal tract. In one aspect, gastrointestinal cancer includes Gastrointestinal stromal tumors (GIST), esophageal cancer, stomach cancer (also called gastric cancer), liver cancer (also called hepatocellular carcinoma, HCC, or hepatoma), gallbladder cancer, pancreatic cancer, colorectal cancer (e.g., called colon cancer, bowel cancer, and rectal cancer) and anal cancer. In one aspect, gastrointestinal cancer includes esophageal cancer, stomach cancer, liver cancer and colorectal cancer. In another aspect, gastrointestinal cancer includes stomach cancer and colorectal cancer.

In another aspect, the cancer patient has a cancer that is generally subjected to 5-FU treatment or is suitable to be treated by 5-FU. In one aspect, cancer is liver cancer such as hepatocellular cancer, gastric cancer, colorectal cancer or breast cancer.

Methods of determining the methylation status of a DNA sequence is described above and further in the experimental examples. Methods of determining gene expression levels are known in the art. For the purpose of illustration only, such methods can include determining the amount of a mRNA transcribed from the gene using, for example, a method comprising, or alternatively consisting essentially of, or yet further consisting of, one or more of in situ hybridization, PCR, real-time PCR, or microarray. The methods can be performed on at least one of a fixed tissue, a frozen tissue, a biopsy tissue, a resection tissue, a microdissected tissue, or combinations thereof. Methods of determining protein expression levels are also known in the art, such as, without limitation, immunohistochemistry, ELISA or protein microarrays.

In addition, knowledge of the identity of the expression level of a gene in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. The identity of the genotype or expression patterns of individual patients can then be compared to the genotype or expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

The methods described herein may be performed, for example, by utilizing pre-packaged diagnostic kits, such as those described below, comprising at least one probe or primer nucleic acid described herein, which may be conveniently used, e.g., to determine whether a subject is likely to experience tumor recurrence following therapy as described herein or has or is at risk of developing disease such as colon cancer.

Diagnostic procedures can also be performed in situ directly upon tissue sections (fixed and/or frozen) of primary tissue such as biopsies obtained from biopsies or resections, such that no nucleic acid purification is necessary. Nucleic acid reagents can be used as probes and/or primers for such in situ procedures (see, for example, Nuovo, G. J. (1992) PCR IN SITU HYBRIDIZATION: PROTOCOLS AND APPLICATIONS, RAVEN PRESS, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

Methods and Compositions of Treatment

This disclosure also provides a method for treating a cancer patient selected for therapy based on the presence of a genetic characteristics as described above, comprising administering an effective amount of a therapy to the patient, wherein the patient is identified by a method described above as suitable for the therapy, thereby treating the patient. For those determined to be likely not suitable for the therapy, alternative treatment methods can be used.

The term "treating" as used herein is intended to encompass curing as well as ameliorating at least one symptom of the condition or disease. For example, in the case of cancer, a response to treatment includes a reduction in tumor mass, increase in survival time, elongation in time to tumor progression, reduction in tumor mass, reduction in tumor burden and/or a prolongation in time to tumor metastasis, time to tumor recurrence, tumor response, complete response, partial response, stable disease, progressive disease, progression free survival, overall survival, each as measured by standards set by the National Cancer Institute and the U.S. Food and Drug Administration for the approval of new drugs. See Johnson et al. (2003) J. Clin. Oncol. 21(7):1404-1411.

"A therapeutically effective amount" or "an effective amount" intends to indicate the amount of a compound or agent administered or delivered to the patient which is most likely to result in the desired response to treatment. The amount is empirically determined by the patient's clinical parameters including, but not limited to the stage of disease, age, gender, histology, sensitivity, toxicity and likelihood for tumor recurrence.

Treatment of Patients Selected as Suitable for the 5-FU Therapy

In one aspect, the patient is determined to be able to exhibit positive clinical outcomes for the 5-FU treatment, based on the examination of the miR-193a-3p/E2F1/SRSF2/caspase pathway genes.

Accordingly, one embodiment of the present disclosure provides a method for treating a cancer patient, comprising administering to the patient an effective amount of a therapy comprising 5-FU, wherein the patient is selected for the therapy based on the presence of one, or two, or three, or four or more of:

(f) methylation of one or more CpG sites associated with the miR-193a gene, (g) decreased expression level of the miR-193a-3p RNA, (h) increased mRNA or protein expression level of the E2F1 gene, (i) increased mRNA or protein expression level of the SRSF2 gene, or (j) increased ratio between the L-form transcript and the S-form transcript of the caspase 2 gene in a tumor sample isolated from the patient, and wherein the increase or decrease is as compared to a control patient that has the same cancer and is resistant to the therapy.

Types of cancers, therapies and samples suitable for practice these methods are described above.

In one aspect, the therapy further comprises radiation therapy.

Treatment of Patients Determined to Exhibit Unfavorable Clinical Outcomes Following a 5-FU Therapy It is contemplated that some patients would exhibit genetic characteristics indicative of unfavorable clinical outcomes if treated with 5-FU because the tumor cells may not be sensitive enough to the treatment. For such patients, a co-administration of an agent that targets the miR-193a-3p/E2F1/SRSF2/caspase pathway so as to render the tumor sensitive to the 5-FU therapy is appropriate.

Accordingly, one embodiment of the disclosure provides a method of treating a cancer patient comprising administering to the cancer patient a therapeutically effective amount of a 5-FU and a therapeutically effective amount of an agent that (i) induces the methylation of the miR-193a gene, (ii) inhibits the biological activity of the miR-193a-3p RNA, (iii) enhances the biological activity of the E2F1 gene, (iv) enhances the biological activity of the SRSF2 gene, or (v) increases the ratio between the L-form transcript and the S-form transcript of the caspase 2 gene.

In one aspect, the patient is selected for the therapy based on the presence of none of:

(f) methylation of the one or more CpG sites associated with the miR-193a gene, (g) decreased expression level of the miR-193a-3p RNA, (h) increased mRNA or protein expression level of the E2F1 gene, (i) increased mRNA or protein expression level of the SRSF2 gene, or (j) increased ratio between the L-form transcript and the S-form transcript of the caspase 2 gene in a tumor sample isolated from the patient, wherein the increase or decrease is as compared to a control patient that has the same cancer and is resistant to 5-FU. In some aspects, the agent is administered concurrently with the 5-FU. In other aspects, the agent is administered prior to or following the administration of 5-FU. When the agent is administered prior to the administration of 5-FU, the agent can be administered at least about 1 hour, 2 hours, 4 hours, 6 hours, 12 hours, 1 day, 2 days, 3 days, 4 days, 5 days, or 6 days prior to the administration of the 5-FU.

Agents that (i) induce the methylation of the miR-193 gene, (ii) inhibit the biological activity of the miR-193a-3p RNA, (iii) enhance the biological activity of the E2F1 gene, (iv) enhance the biological activity of the SRSF2 gene, or (v) increase the ratio between the L-form transcript and the S-form transcript of the caspase 2 gene can be readily prepared and examples are provided in the experimental example, such as miR-193a-3p antagomir.

Inhibiting or enhancing the "biological activity" of a gene, a protein, or an RNA, as used herein, includes without limitation inhibiting or enhancing the expression, the protein or RNA activity, the proper localization or modification of the gene, protein, or RNA molecules.

Generally, such agents include one type that activates the activity or expression of a gene or gene product (e.g., E2F1, SRSF2 and L-form of caspase 2) and another type that represses the activity or expression of a gene or gene product (e.g., miR-193a-3p, S-form of caspase 2). Methods of designing and preparing both types of agents are well known in the art and briefly described below. Moreover, an agent that specifically induces methylation of a gene can also be readily prepared with known methods.

Non-limiting examples of such agents include a miR-193-3p antagomir, an E2F1 protein or a polynucleotide encoding the E2F1 protein, an SRSF2 protein or a polynucleotide encoding the SRSF2 protein, an L-form caspase 2 protein or a polynucleotide encoding the L-form caspase 2 protein, or an siRNA directed at the S-form transcript of caspase 2.

Also provided is a composition comprising a 5-FU and an agent that
 (i) induces the methylation of the miR-193a gene,
 (ii) inhibits the biological activity of the miR-193a-3p RNA,
 (iii) enhances the biological activity of the E2F1 gene,
 (iv) enhances the biological activity of the SRSF2 gene, or
 (v) increases the ratio between the L-form transcript and the S-form transcript of the caspase 2 gene.

Also provided are kits or packages that comprises a 5-FU and an agent that
 (i) induces the methylation of the miR-193a gene,
 (ii) inhibits the biological activity of the miR-193a-3p RNA,
 (iii) enhances the biological activity of the E2F1 gene,
 (iv) enhances the biological activity of the SRSF2 gene, or
 (v) increases the ratio between the L-form transcript and the S-form transcript of the caspase 2 gene. Methods of using the compositions, kits, packages, for treating cancer is also provided.

Methods for Inducing Methylation of a Gene in a Cell

Methods of site-specific changing the DNA methyaltion state, e.g., the methylation status at certain CpG site of the miR-193a gene, are known in the art. For instance, Xu and Bestor (Xu et al. (1997) Nat Genet, 17, 376-378) describe a method to specifically induce CpG methylation targeted at a predetermined sequence. As the genomic sequence of the miR-193a gene is known and the CpG sites, which when methylated can suppress the expression of the miR-193a-3p RNA, have been disclosed and examined in the present experimental example, Xu and Bestor's method can readily adopted to induce, in vitro or in vivo, methylation of these CpG sites leading to decreased expression of the miR-193a-3p RNA.

Methods for Decreasing the Biological Activity of a Gene in a Cell

An agent that decreases the biological activity of a gene, such as miR-193a-3p can be a antagomir, or a siRNA, a ribozyme, without limitation.

Antagomirs are a class of chemically engineered oligonucleotides and can be used to silence endogenous microRNA. An antagomir is a small synthetic RNA that is perfectly complementary to the specific miRNA target with either mispairing at the cleavage site of Ago2 or some sort of base modification to inhibit Ago2 cleavage. Usually, antagomirs have some sort of modification, such as 2' methoxi groups and phosphothioates, to make it more resistant to degradation. Methods of designing and using antagomirs are known in the art, see, Kriitzfeldt et al., (2005). *Nature* 438 (7068): 685-9.

Methods for Increasing the Activity or Expression of a Gene in a Cell

Methods for increasing the level of a protein, or polypeptide or peptide, such as SRSF2, in a cell are known in the art. In one aspect, the SRSF2 level is increased by increasing the amount of a polynucleotide encoding SRSF2, as provided above, wherein that polynucleotide is expressed such that new SRSF2 is produced. In another aspect, increasing the SRSF2 level is increased by increasing the transcription of a polynucleotide encoding SRSF2, or alternatively translation of SRSF2, or alternatively post-translational modification, activation or appropriate folding of SRSF2. In yet another aspect, increasing SRSF2 level is increased by increasing the binding of the protein to appropriate cofactor, receptor, activator, ligand, or any molecule that is involved in the protein's biological functioning. In some embodiments, increasing the binding of SRSF2 to the appropriate molecule is increasing the amount of the molecule. In one aspect of the embodiments, the molecule is the SRSF2 protein. In another aspect of the embodiments, the molecule is a small molecule. In a further aspect of the embodiments, the molecule is a polynucleotide.

Methods of increasing the amount of polynucleotide in a cell are known in the art and can be modified for increasing the amount of a polynucleotide encoding SRSF2. In one aspect, the polynucleotide can be introduced to the cell and expressed by a gene delivery vehicle that can include a suitable expression vector.

Suitable expression vectors are well-known in the art, and include vectors capable of expressing a polynucleotide operatively linked to a regulatory element, such as a promoter region and/or an enhancer that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors include those that are replicable in eukaryotic cells and/or prokaryotic cells and those that remain episomal or those which integrate into the host cell genome.

As used herein, the term "vector" refers to a non-chromosomal nucleic acid comprising an intact replicon such that the vector may be replicated when placed within a cell, for example by a process of transformation. Vectors may be viral or non-viral. Viral vectors include retroviruses, adenoviruses, herpesvirus, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

Non-viral vector may include plasmid that comprises a heterologous polynucleotide capable of being delivered to a target cell, either in vitro, in vivo or ex-vivo. The heterologous polynucleotide can comprise a sequence of interest and can be operably linked to one or more regulatory elements and may control the transcription of the nucleic acid sequence of interest. As used herein, a vector need not be capable of replication in the ultimate target cell or subject. The term vector may include expression vector and cloning vector.

Gene delivery vehicles also include DNA/liposome complexes, micelles and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., a cell surface marker found on stem cells or cardiomyocytes. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins of this invention are other non-limiting techniques.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz (1996) Current Opinion in Neurobiology 6:629-634. Another subsequence, the h (hydrophobic) domain of signal peptides, was found to have similar cell membrane translocation characteristics (see, e.g., Lin et al. (1995) J. Biol. Chem. 270:14255-14258). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

Methods of delivering a protein to a cell, either to increase the biological activity of itself or a protein positively regulated by this protein, or to decrease the biological activity of a protein negatively regulated by this protein, are generally known in the art. For example, SRSF2 can be delivered to a eukaryotic cell by a type III sercreation machine. See, e.g., Galan and Wolf-Watz (2006) Nature 444:567-73. Biologically active and full length protein, for another example, can also be delivered into a cell using cell penetraint peptides (CPP) as delivery vehicles. The trans-activating transcriptional activator (TAT) from human immunodeficiency virus 1 (HIV-1) is such a CPP, which is able to deliver different proteins, such as horseradish peroxidase and RNase A across cell membrane into the cytoplasm in different cell lines. Wadia et al. (2004) Nat. Med 10:310-15. Accordingly, in one aspect, SRSF2 can be delivered to a cell using TAT as a vehicle to increase the biological activity of SRSF2 in the cell.

Liposomes, microparticles and nanoparticles are also known to be able to facilitate delivery of proteins or peptides to a cell by encapsulating the peptides (reviewed in Tan et al. (2010) Peptides 31(1):184-93). The liposomes, microparticles or nanoparticles can also comprise a targeting antibody or fragment thereof can be used in the methods of this invention. To enhance delivery to a cell, the proteins can be conjugated to antibodies or binding fragments thereof which bind cell surface antigens, e.g., a cell surface marker found on progentior cells.

In another aspect, non-covalent method which forms CPP/protein complexes has also been developed to address the limitations in covalent method such as chemical modification before crosslinking and denaturation of proteins before delivery. For example, a short amphipathic peptide carrier, Pep-1 and protein complexes have proven effective for delivery. It was shown that Pep-1 could facilitate rapid cellular uptake of various peptides, proteins and even full-length antibodies with high efficiency and less toxicity. Cheng et al. (2001) Nat. Biotechnol. 19:1173-6.

The therapies can be administered by any suitable formulation. Accordingly, a formulation comprising the necessary therapy is further provided herein. The formulation can further comprise one or more preservatives or stabilizers. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3, 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

The chemotherapeutic agents or drugs can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this disclosure, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", 52$^{nd}$ ed., Medical Economics, Montvale, N.J. (1998).

Many combination chemotherapeutic regimens are known to the art, such as combinations of platinum compounds and taxanes, e.g. carboplatin/paclitaxel, capecitabine/docetaxel, the "Cooper regimen", fluorouracil-levamisole, fluorouracil-leucovorin, fluorouracil/oxaliplatin, methotrexate-leucovorin, and the like.

Combinations of chemotherapies and molecular targeted therapies, biologic therapies, and radiation therapies are also well known to the art; including therapies such as trastuzumab plus paclitaxel, alone or in further combination with platinum compounds such as oxaliplatin, for certain breast cancers, and many other such regimens for other cancers; and the "Dublin regimen" 5-FU IV over 16 hours on days 1-5 and 75 mg/m$^2$ cisplatin IV or oxaliplatin over 8 hours on day 7, with repetition at 6 weeks, in combination with 40 Gy radiotherapy in 15 fractions over the first 3 weeks) and the "Michigan regimen" (fluorouracil plus cisplatin or oxaliplatin plus vinblastine plus radiotherapy), both for esophageal cancer, and many other such regimens for other cancers, including colorectal cancer.

In another aspect of the disclosure, the method for treating a patient further comprises, or alternatively consists essentially of, or yet further consists of surgical resection of a metastatic or non-metastatic solid malignant tumor and, in some aspects, in combination with radiation. Methods for treating these tumors as Stage I, Stage II, Stage III, or Stage IV by surgical resection and/or radiation are known to one skilled in the art. Guidelines describing methods for treatment by surgical resection and/or radiation can be found at the National Comprehensive Cancer Network's web site, nccn.org, last accessed on May 27, 2008.

The disclosure provides an article of manufacture, comprising packaging material and at least one vial comprising a solution of the chemotherapy as described herein and/or or at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The disclosure further comprises an article of manufacture, comprising packaging material, a first vial comprising the chemotherapy and/or at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

Chemotherapeutic formulations of the present disclosure can be prepared by a process which comprises mixing at least one antibody or biological equivalent and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include those pen-injector devices for delivery of a solution such as BD Pens, BD Autojectore, Humaject® NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, MediJect®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at weston-medical.com), Medi-Ject Corp (Minneapolis, Minn., available at mediject.com).

Various delivery systems are known and can be used to administer a chemotherapeutic agent of the disclosure, e.g., encapsulation in liposomes, microparticles, microcapsules, expression by recombinant cells, receptor-mediated endocytosis. See e.g., Wu and Wu (1987) J. Biol. Chem. 262: 4429-4432 for construction of a therapeutic nucleic acid as part of a retroviral or other vector, etc. Methods of delivery include but are not limited to intra-arterial, intra-muscular, intravenous, intranasal and oral routes. In a specific embodiment, it may be desirable to administer the pharmaceutical compositions of the disclosure locally to the area in need of treatment; this may be achieved by, for example, and not by way of limitation, local infusion during surgery, by injection or by means of a catheter.

The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

Also provided is a therapy or a medicament comprising an effective amount of a chemotherapeutic as described herein for treatment of a human cancer patient having the appropriate expression level of the gene of interest as identified in the experimental examples. Further provided is a therapy comprising a platinum drug, or alternatively a platinum drug therapy, for use in treating a human cancer patient having the appropriate expression level of the gene of interest as identified in the experimental examples.

Methods of administering pharmaceutical compositions are well known to those of ordinary skill in the art and include, but are not limited to, oral, microinjection, intravenous or parenteral administration. The compositions are intended for topical, oral, or local administration as well as intravenously, subcutaneously, or intramuscularly. Administration can be effected continuously or intermittently throughout the course of the treatment. Methods of determining the most effective means and dosage of administration are well known to those of skill in the art and will vary with the cancer being treated and the patient and the subject being treated. Single or multiple administrations can be carried out with the dose level and pattern being selected by the treating physician.

Kits, Reagent Panels or Packages

As set forth herein, the disclosure provides diagnostic methods for determining the gene expression of interest. In some embodiments, the methods use probes or primers or microarrays comprising nucleotide sequences which are complementary to the gene of interest. Accordingly, the disclosure provides kits for performing these methods as well as instructions for carrying out the methods of this disclosure. Thus, in one aspect, this disclosure also provides a kit for use in identifying an adjuvant cancer patient more likely to have tumor recurrence, comprising, or alternatively consisting essentially of, or yet further consisting of, suitable antibodies, primers, probes and/or a microarray for determining the methylation status or expression of the miR-193a-3p/E2F1/SRSF2/caspase pathway genes, and instructions for use therein. Examples of suitable primers and probes are provided herein.

The kits can include all or some of the positive controls, negative controls, reagents, primers, sequencing markers, probes and antibodies described herein for determining the subject's genotype in the polymorphic region of the gene of interest. In some aspects, the kits also include a therapy for treating the identified or selected patient.

As amenable, these suggested kit components may be packaged in a manner customary for use by those of skill in the art. For example, these suggested kit components may be provided in solution or as a liquid dispersion or the like.

This disclosure also provides for a prognostic panel of genetic markers selected from, but not limited to the probes and/or primers to determine DNA methylation gene expression as identified herein. The probes or primers can be attached or supported by a solid phase support such as, but not limited to a gene chip or microarray. The probes or primers can be detectably labeled.

Primers or probes can be affixed to surfaces for use as "gene chips" or "microarray." Such gene chips or microarrays can be used to detect expression variations by a number of techniques known to one of skill in the art. In one technique, oligonucleotides are arrayed on a gene chip for determining the DNA expression or by the sequencing by hybridization approach, such as that outlined in U.S. Pat. Nos. 6,025,136 and 6,018,041. The probes of the disclosure also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Thus, one embodiment of the disclosure provides a kit, a reagent panel, or a package comprising one, or two, or three, or four sets of agents, each set selected from a different group of:

(1) primer, probe or antibody for determining the methylation status of the miR-193a gene or the expression level of the miR-193a-3p RNA, (2) primer, probe or antibody for determining the expression level of the E2F1 gene, (3) primer, probe or antibody for determining the expression level of the SRSF2 gene, or (4) primer, probe or antibody for determining the amount or ratio of the L-form transcript and the S-form transcript of the caspase 2 gene.

The disclosure now being generally described, it will be more readily understood by reference to the following example which is included merely for purposes of illustration of certain aspects and embodiments of the present disclosure, and are not intended to limit the disclosure.

Experimental Details

Example 1

This example shows that DNA methylation repressed the expression of miR-193a-3p leading to increased sensitivity of cancer cells to 5-FU treatments, via an miR-193a-3p/E2F1/SRSF2/caspase pathway. Such correlation is then confirmed with mechanistic studies. Treatment methods for those in which the expression of miR-193a-3p is not repressed who are thus resistant to 5-FU treatment are then tested, which methods involve a gene therapy targeting the miR-193a-3p/E2F1/SRSF2/pathway.

Methods and Materials

Analysis at the Cellular Level—

Human HCC cell lines were obtained from the Cell Bank: QGY-7703 (Cell Bank in Shanghai, China, No: TCHu43) (He L. et al. (1984) In vitro, 20, 493-504), SMMC-7721 (Cell Bank in Shanghai, China, No: TCHu52), BEL-7402 (Cell Bank in Shanghai, China, No: TCHu10), HepG2 (ATCC No. HB-8065), Hep3B (ATCC No. HB-8064), PLC (ATCC No. CRL-8024) and FOCUS and human breast cell lines: MDAMB-231, MDAMB-468, Bcap-37, ZR-75-30, MCF-7 and ZR-75-1.

The log phase of cell culture was obtained in Dulbecco modified Eagle medium (Invitrogen) containing 10% calf serum and 1% streptomycin-penicillin at 37° C. in 5% $CO_2$. The thiazolyl blue tetrazolium blue (MTT)-based cell proliferation assay was carried out as follows: $5 \times 10^3$ to $1 \times 10^4$ cells in triplicate were cultured into each well of a 96-well plate (in triplicate) for 72 h, followed by a 3-h 37° C. incubation after addition of 10 µL (5 mg/mL) MTT salt (Sigma, USA). The OD 570-nm reading was obtained; the mean and SD of the triplicate experiments were calculated and plotted (Fei Q. et al. (2008) Acta Biochim Biophys Sin (Shanghai), 40, 466-477).

To determine the $IC_{50}$, cells in triplicate were subjected to a series dilution of each drug for 72 h, followed the MTT-based analysis. The relative OD 570-nm readings (mean and SD) in each drug-treated set and the no-drug mock sample were calculated (%) and plotted against the logarithm of the drug concentration. The linear regression parameters were determined for each curve and the $IC_{50}$ extrapolated (Andrisano V. et al. (2001) J Chromatogr B Biomed Sci Appl, 753, 375-383). Sources of the drugs are as follows: 5-FU, Shanghai Xudong Haipu Pharmaceutical, China; gemcitabine, Jiangsu Hansen Pharmaceutical, China; epirubicin, Shenzhen Main Luck Pharmaceutical, China; irinotecan, Aventis Pharmaceutical, Germany; paclitaxel, Bristol-Myers Squibb, USA; mitomycin, Hisun Pharmaceutical, China); docetaxel, Jiangsu Hengrui Medicine, China; vinorelbine, Yangzhou Aosaikang Pharmaceutical, China; and cisplatin, Qilu Pharmaceutical Factory, China.

Luciferase reporter assay—The seed sequences (miR-193a-3p: 5'-AATT TGGGTCTTTGCGGGCGAGATGAT-3',3'-CTAGATCATCTCGCCCGCAAAGACCCA-5'; miR-127-3p: 5'-AATTCTGAAGCTCAGAGGGCTCTGATT-3', 3'-CTAGAATCAGAGCCCTCTGAGCTTCAG-5' (Invitrogen, USA) were annealed and inserted into the EcoRI and XbaI sites of the CMV promoter driven fly luciferase reporter, pCDNA3.1-luc (Promega, USA), to make miR-193a-3p-luc and pGL3-miR-127-3p-luc luciferase reporter constructs, respectively. The analysis mediated with Lipofectamine 2000 transfection/reporter was performed as previously described (Zhang J. et al. (2004) Cell Res, 14, 283-294). The culture at 60% confluence in duplicate was transfected by one luciferase reporter 25 ng/50 ng carrier plasmid DNA/5 ng CMV-Renilla luciferase (to control the transfection efficacy); luciferase activities of the transfected cells were measured after 24 h with a dual luciferase reporter system (Promega, Madison, Wis.) by MiniLumat LB 9506 (Berthold, Germany). The SD of the ratio of the firefly luciferase over the Renilla luciferase activity of the duplicates was plotted against the tested constructs. All the experiments were carried out at least three times, and the result from one representative experiment was presented (Zhang J. et al. (2004) Cell Res, 14, 283-294).

The miR-193a-3p mimic and antagomir (Ribobio, Guangzhou, China) transfection was performed at dose of 10 and 50 nM, respectively. For the cell cycle profiling, cells were seeded in 6-well plates at 40% confluence and incubated at 37° C. for 24 h before transfection with the mock (non-related mimic or antagomir), miR-193a-3p mimic, or antagomir with miR-193a-3p-luc reporter/CMV-Renilla reporter constructs. The transfected cells were collected and fixed by 70% ethanol at −20° C. for 24 h, stained with 50 µg/mL propidium iodide (Sigma, USA), and analyzed on a fluorescence-activated cell sorter (FACS) according to the manufacturer's instructions (Becton Dickinson). All flow cytometry experiments were performed at least three times and a representative experiment was shown.

Analyses at Molecular Levels—

Protein: Cells were lysed by the 1×SDS loading buffer (60 mM Tris-HCl, pH 6.8; 2% SDS; 20% glycerol; 0.25% bromophenol blue; 1.25% 2-mercaptoethanol) and then sonicated to shear the genomic DNA (Bioruptor, Diagenode, Belgium)/Western blot-analyzed with antibodies: anti-SRSF2 (AP2800a), anti-E2F1 (AP7593a), anti-E2F6 (AP6637c), anti-YWHAZ (AP8152c), anti-HDAC1 (AP1101a), anti-MCL1(AP1312a), anti-PCNA(AP2835b), anti-PHF8(AP9276b), anti-TYSY (AP6682b), anti-PTK2 (AP8614b), anti-CDCSL (AP8949c) (Abgent, USA), and anti-β-actin (Sigma, USA), respectively. The target proteins were then probed with anti-rabbit IgG peroxidase-conjugated antibody (KangChen Bio-tec, Shanghai, China) and followed by an enhanced chemoluminescence reaction (Pierce, USA). The relative levels of proteins were quantified by densitometry with the FR-200 Analysis System (Fu-Ri Technology, Shanghai, China).

RNA: Total RNA was isolated using TRIzol reagent (Invitrogen, USA). Complementary DNA synthesis was performed using a primeScript RT reagent kit (Tiangen Biotech Co., Ltd., Beijing, China) for the SYBR® Green-based real-time PCR analysis in Rotor-Gene™ 6000 system, Qiagen, Germany) of SRSF2, E2F1, ABCC8, and CASP2S/L. The expression of miR-193a-3p (Ribobio, Guangzhou, China) was assessed using the 2-Ct method with RNA content normalized to the U6 RNA (Ribobio, Guangzhou, China) and to β-actin for other genes and plotted. The high-throughput, quantitative nuclease protection based analysis (Bourzac K. M. et al. (2011) J Biotechnol, 154, 68-75; Pechhold S. et al. (2009) Nat Biotechnol, 27, 1038-1042) on a customized array that are designed for the simultaneous determination of the expression of 42 human miRs and 5 housekeeping genes was determined. Only miR-193a-3p expression was shown.

DNA: Genomic DNA was isolated by a standard phenol/chloroform purification method and qualified by electrophoresis on an agarose gel and visualized with ethidium bromide. For DNA methylation analysis, the primer pairs for methylation-specific PCR (MSP) and bisulfite specific PCR (BSP) was designed according to MethPrimer (see www.urogene.org/methprimer/indexl.html) (Table 1). The methylation status of the miR-193a gene locus was carried out by bisulfate conversion and PCR analyses were as described previously (Yu J. et al. (2007) Clin Cancer Res, 13, 7296-7304).

TABLE 1

PCR Primers used in this example

| Name | Tm (° C.) | Sequence | Purpose |
| --- | --- | --- | --- |
| ACTBREALf | 56 | TCACCCACACTGTGCCCATCT ACGA | qRT-PCR |
| ACTBREALt |  | CAGCGGAACCGCTCATTGCCA ATGG |  |
| E2F1f | 58 | CACAGATCCCAGCCAGTCTCTA | qRT-PCR |
| E2F2t |  | GAGAAGTCCCGCACATG |  |
| SRFS2f | 58 | CCACTCAGAGCTATGAGCTACG | qRT-PCR |
| SRFS2t |  | ACTCCTTGGTGTAGCGATCC |  |

TABLE 1-continued

PCR Primers used in this example

| Name | Tm (° C.) | Sequence | Purpose |
|---|---|---|---|
| CASP2Lrf | 64 | CCTGCCGTGGAGATGAGA | qRT-PCR |
| CASP2rt | | TCGCCAACTTTTCTTTACCG | |
| CASP2Srf | | CTTGGGCACCTGCCTTCTGT | |
| ABCC8rtf | 56 | GGTGACCGAATCCCACCATC | qRT-PCR |
| ABCC8rtt | | CAGGGCAATTAGCAGCTTGG | |
| miR-193a_mf | 58 | GGGGACGTATTTCGAATTTC | MSP |
| miR-193a_mt | | TAAAAAACAACCTAACCGAAACG | |
| miR-193a_uf | 56 | GGGGATGTATTTTGAATTTTGA | MSP |
| miR-193a_ut | | ACACACACCAACCCAAAAA | |
| miR-193a_bspf | 50 | GTTTGAGGGATATTTAGAGTTT | BSP |
| miR-193a_bspt | | ACCTAAAAAACAACCTAACC | |

The CpG methylome was established by probing the heavily methylated DNA fraction enriched by the methylated DNA-binding domain (MBD) of the rat Mecp2 (Brinkman A. B. et al. (2010) Methods, 53, 232-236) [to the Nimblegen customized CpG island array (0.38 million probes) and validated by bisulfite sequencing as previously described (Brinkman A. B. et al. (2010) Methods, 53, 232-236; Li Y. et al. (2010) PLoS Biol, 8, e1000533) Solexa sequencing-based miR expression profiling was provided by BGI (Shenzhen, China).

In Vivo Study—

After transfection with 50 nM miR-193a-3p or mock antagomirs (Ribobio, China) for 24 h, SMMC-7721 cells were collected and subcutaneously injected into the left and right flanks (1 25×10$^6$ cells/point) of each nude mouse (10 total), respectively. On day 12 after cell injection, 5 mice received 5-FU (75 mg/kg mouse body weight) intraperitoneal and then twice again in 1 week. The remaining 5 mice received phosphate-buffered saline (PBS) as a mock treatment control. And at the same time, the right side of all mice tumor were intratumorally injected with miR-193a-3p antagomir and left side with mock antagomir (according to manufacture instruction, Ribobio). To monitor the tumor growth, the volume was measured with a Vernier caliper on days 12, 18, 25, and 32 and calculated as Volume=$W^2 \times L \times 0.5$ (W and L represent the largest and next largest tumor diameters [cm]) and then plotted. Mice were humanely sacrificed on day 32, and tumors were weighed and photographed. Immunostaining was performed for ki67, SFS2, and E2F1 expression in both tumors of mouse number 4 (mock treated) mouse number 6 (5-FU treated).

Expressions of SRSF2, E2F1, and Ki67 proteins were measured by immunochemical analysis on 5-mm slices of formalin-fixed paraffin-embedded tumor xenografts in nude mice. Antigen were retrieved by pretreating dewaxed sections in a microwave oven at 750 W for 5 min in citrate buffer (pH 6) and processed with a Super Sensitive Link-Labeled Detection System (Biogenex, Menarini, Florence, Italy). The enzymatic activity was developed using 3-amino-9-ethylcarbazole (Dako, Milan, Italy) as a chromogenic substrate. Following counterstaining with Mayer hematoxylin, slides were mounted in aqueous mounting medium (glycergel, Dako). The relative level of each protein was calculated as the density score (mean intensity/lasso, TAMJ reads) that was determined using TMAJ software (http://tmaj.pathology.jhmi.edu/), and the percentage of the TMAJ reads of mock over the antagomir-transfected tumor was calculated and plotted.

Statistical Analysis—

Data are presented as mean and error bars indicate the standard deviation (s.d.) or the standard error (s.e.m.). All statistical analyses were performed with Excel (Microsoft) or Prism (GraphPad). Two-tailed Students t test, a one-way analysis of variance (ANOVA) or Mann-Whitney U test was used to calculate statistical significance. A P value <0.05 was considered to be significant.

Results

DNA Methylation-Regulated miR-193a-3p Expression Correlates 5-FU Resistance of SMMC-7721 and QGY-7703

The chemoresistance of eight HCC cell lines were determined by $IC_{50}$ profiling: QGY-7703, SMMC-7721, YY-8103, PLC, HepG2, BEL-7402, Hep3B, and FOCUS to gemcitabine, 5-FU, cisplatin, vinorelbine, docetaxel, mitomycin, paclitaxel, ironotecan, and epirubicin, respectively. The $IC_{50}$ difference among HCC cell lines to vinorelbine, docetaxel, mitomycin, paclitaxel, and epirubicin was no more than 17-fold (FIG. 1A). However, the $IC_{50}$ to 5-FU of QGY-7703 was approximately 105.2-fold ($IC_{50}$: 0.39 vs. 41.01 μg/mL) lower than that of SMMC-7721, whereas their $IC_{50}$ to each of the remaining therapeutics differed little (FIG. 1B, C).

HepG2 was the 2$^{nd}$ 5-FU sensitive HCC cell line ($IC_{50}$: 1.45 μg/mL, 27.3-fold lower than SMMC-7721, FIG. 2A) in this group, with other five members even more resistant to 5-FU than SMMC-7721 (the data of four cell lines shown in FIG. 2B). Therefore, the genomic profiling at both DNA methylation and miR expression levels was carried out on both QGY-7703 and SMMC-7721 to seek for the key DNA methylation regulated miRs that specifically commend the 5-FU resistance of HCC cells. Among 39 differentially expressed miRs that were identified by a Solexa sequencing-miRomic analysis (unpublished observation), miR-193a-3p was one of the most differentially expressed in between SMMC-7721 and QGY-7703: 11.21 fold higher in former than in the later by Solexa sequencing (FIG. 1D) and 4.44 fold higher by qRT-PCR based validation (FIG. 1E). miR-193a-3p level was also low in another 5-FU sensitive HCC cell line, HepG2 (the 2$^{nd}$ 5-FU sensitive cell line), but high in all other 5-FU-resistant cell lines: PLC, FOCUS, Hep3B and BEL-7402 (FIG. 2C).

This example also established the methylomic profiles of both cell lines by probing a customized Nimblegene 0.38 million oligonucleotide CpG island array with the heavily methylated DNA fraction from an MBD domain-based capture procedure. The miR-193a gene was at the top of the most differentially methylated CpG islands (>3000, unpublished observation): hypermethylated in QGY-7703 and hypomethylated in SMMC-7721 (methylation index: +1.22 vs. −2.35; FIG. 1F), negatively correlating with the miR-193a-3p expression. This example further determined the methylation state of the miR-193a gene by BSP and MSP of these two HCC cell lines and the other five HCC cell lines, and showed that miR-193a hypermethylated in both 5-FU-sensitive cell lines: HepG2 and QGY-7703, but unmethylated or barely methylated in all the five 5-FU-resistant cell lines, including SMMC-7721 (FIG. 2D-F). The DNA methylation state dependence of miR-193a transcription was finally confirmed by showing that 5-Aza-2'-deoxycytidine mediated demethylation raised the steady state level of miR-193a-3p in QGY-7703 (FIG. 3). It is evident that HCC's 5-FU sensitivity is tightly linked to the DNA methylation regulated miR-193a-3p expression in HCC.

Both SRSF2 and E2F1 Genes are Bona Fide Targets of miR-193a-3p

To determine whether differentially expressed miR-193a-3p do have functional impact, this example transfected both cell lines with each of three luciferase reporter constructs: CMV-luc (empty vector control), its derivatives miR-193a-3p-luc (the testing construct) and miR-127-luc (a non-specific control). The latter two have each's target sequences inserted at the 3' end of the luciferase genes, respectively (FIG. 4A). Well correlating with the level of miR-193a-3p, in comparison with each of other reporter, the luciferase activity of the transfected miR-193a-luc was no more than 0.29 fold in SMMC-7721 (a high miR-193a-3p expressing) (FIG. 4B), but was similar in QGY-7703 (a miR-193a-3p low expressing) (FIG. 4C).

To identify the target gene(s), expression of which is repressed by miR-193a-3p at the post transcriptional level, this example performed Western blot analysis of ten proteins in both HCC cell lines. The following five proteins were selected from 141 bioinformatically predicted miR-193a-3p target genes (http://www.targetscan.org and http://www.ebi.ac.uk/astd): E2F transcription factor 1 (E2F1), E2F transcription factor 6 (E2F6), tyrosine 3-monooxygenase/tryptophan 5-monooxygenase activation protein, zeta polypeptide (YWHAZ), serine/arginine-rich splicing factor 2 (SRSF2), and myeloid cell leukemia sequence 1 (BCL2-related, MCL1). This example also selected thymidylate synthetase (TYSY) for its role in 5-FU metabolism, PTK2 protein tyrosine kinase 2 (PTK2) for its role in cell motility and survival, histone deacetylase 1 (HDAC1) for its involvement in protein acetylation regulation, and both proliferating cell nuclear antigen (PCNA) and CDC5 cell division cycle 5-like (CDC5L) for their functional coupling with SRSF2 that is suggested bioinformatically (http://funcoup.sbc.su.se/). Both SRSF2 and E2F1 (0.02 vs. 1 and E2F1: 0.31 vs. 1, respectively, FIG. 4D), but none of other tested have the expected pattern for a bona fide targets of miR-193a-3p: i.e., low in the miR-193a-3p high expressing SMMC-7721 and high in the miR-193a-3p low expressing QGY-7703. Both mRNA levels were also lower in SMMC-7721 than in QGY-7703 (2-ΔΔCt of SMMC-7721/QGY-7703 for SRSF2: 0.56, E2F1: 0.48, FIG. 4E), in contrast to a similar level of a non miR-193a-3p target: ATP-binding cassette, subfamily C (CFTR/MRP), member 8 (ABCC8) (1.14, FIG. 4E). Taken together, the miR-193a-3p regulation of HCC sensitivity to 5-FU is likely achieved by its regulation of both SRSF2 and E2F1 expression at both mRNA stability and translation levels. Lacking of inter-cellular difference of TYSY level suggested that the 5-FU metabolistic process may not impact to the 5-FU resistance of HCC cells in this study.

Forced Alteration of miR-193a-3p Level Reverse the 5-FU Resistance of HCC Cells

Figure 5:
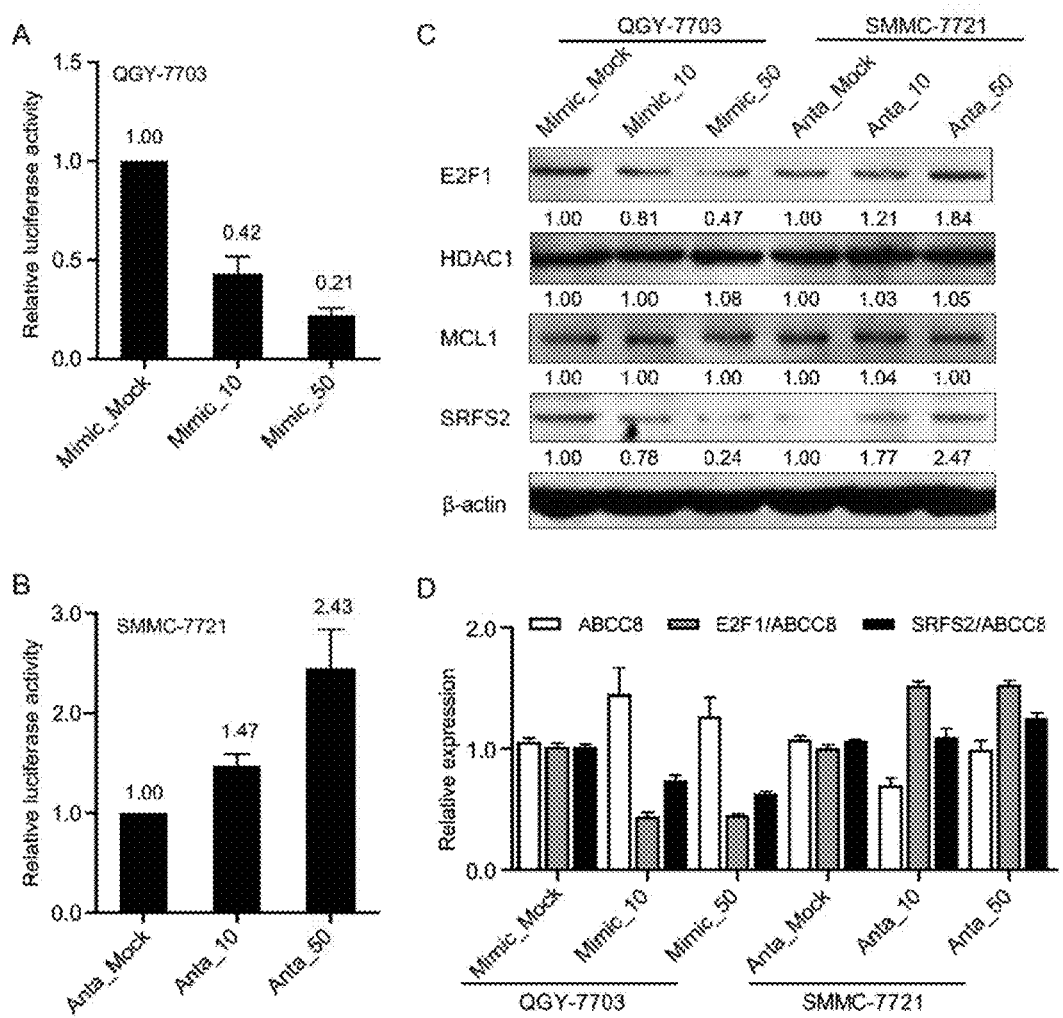
FIG. 5 shows that E2F1 and SRSF2 levels are negatively regulated by miR-193a-3p. QGY-7703 (A) and SMMC-7721 (B) were transfected with miR-193a-3p mimic (10 and 50 nM), antagomir (10 and 50 nM), or mock control (nonspecific, 50 nM) together with miR-193a-3p-luc, and luciferase activities were determined. Relative luciferase activities over the mock (set arbitrarily as 1) were calculated. (C) The protein levels of E2F1, SRSF2, HDAC1, MCL1, and β-actin in mock- and mimic-transfected (QGY-7703) or antagomir-transfected (SMMC-7721) cells were compared by Western blot and digitalized with that in the mock-transfected cells (arbitrarily as 1). (D) The mRNA levels of E2F1, SRSF2, and ABCC8 were determined by qRT-PCR analysis and digitalized with ABCC8 (arbitrarily as 1).

This example raised the miR-193a-3p level by the mimic-transfection and found: 1) the luciferase activity of miR-193a-3p-luc was reduced up to 0.21 (FIG. 5A) and 2) both E2F1 and SRSF2 proteins went down to 0.47 and 0.24 fold, respectively, of the mock mimic-transfected levels in QGY-7703 (FIG. 5C). This example then reduced the miR-193a-3p level by the antagomir transfection and found: 1) the luciferase activity of the miR-193a-3p-luc up to 2.43 (FIG. 3B), and 2) the level of both E2F1 and SRSF2 up to 1.84 and 2.47 fold, respectively, of the mock antagomir transfected levels in SMMC-7721 (FIG. 5C). Neither MCL1 nor HDAC (non-target proteins) protein levels were affected by the same treatments (FIG. 5C), The changes of SRSF2 and E2F1 mRNAs but not ABCC8 mRNA (a non-target control) were also evident (FIG. 5D), indicating of the involvement of miR-193a-3p mediated control of the mRNA stability level. The miR-193a-3p mimic transfection also slowed down QGY-7703 cell proliferation by 27% (1.05 vs. 1.44 for the mock, P=0.0227, FIGS. 6A and C) and induced G1 arrest in QGY-7703 (G1 phase 62.76% vs. 50.71% for the mock, FIG. 6D). More importantly, its 5-FU $IC_{50}$ of was raised by 6.35-fold (5.29 vs. 0.72 μg/mL; FIG. 6E) in comparison with the mock-transfected. SRSF2 responds more profoundly than E2F1 to the changing level of miR-193a-3p (FIG. 5).

In view of the fact that SRSF2 is a direct target of E2F1's transcription regulation and the extra, therefore, comes from the E2F1's impact to the SRSF2 transcription. Then this example carried out siRNA mediated repression of SRSF2 in QGY-7703 to determine whether SRSF2 is the key mediator of the miR-193a-3p's dictation of the 5-FU resistance in HCC. Consistent with its reduction down to the 0.13 level in the mock siRNA transfected (FIG. 6B), QGY-7703 cell proliferation slowed down by 37% (0.66 vs. 1.04, P=0.0323; FIG. 6C), arrested at $G_1$ phase ($G_1$ phase 58.33% vs. 50.11%, P=0.0189; FIG. 6D) and became more resistant to 5-EU ($IC_{50}$ of 5-FU: 2.22 vs. 0.68 μg/mL, FIG. 6E). The further confirmation came from the experiment with the miR-193a-3p antagomir transfected SMMC-7721. In agreement with by 0.62-fold elevation of luciferase activity of co-transfected miR-193a-3p-luc (FIG. 7A), SMMC-7721 cell proliferation accelerated by 33% (1.88 vs. 1.41, P=0.0479, FIG. 7B) and have more cells enter S phase ($G_1$ phase 51.3% vs. 46.6% mock, P=0.0362, FIG. 7C). Most importantly, its 5-FU $IC_{50}$ was reduced by 2.47-fold (46.70 μg/mL vs 13.44 μg/mL, P=0.0251, FIG. 7D). In conclusion, SRSF2 contribute a great part to the miR-193a-3p's negative control of the HCC's resistance to 5-FU.

SRSF2-Mediated Elevation in the Ratio of the Proapoptotic/Antiapoptotic Forms of Caspase 2 Transcripts Underlies 5-FU Sensitivity in HCC Cells It has been suggested that relative levels of the proapoptotic/antiapoptotic splicing forms of apoptotic genes rather than the absolute level of either reflects the apoptotic propensity and therefore chemoresistance of cancer cells. As a key component of spliceosome, SRSF2 preferentially up-regulate the proapoptotic splice forms of apoptotic genes, including CASP8 and FADD-like apoptosis regulator (C-Flip), caspase 8 and 9, apoptosis-related cysteine peptidase (Caspase-8 and -9), and apoptosis regulator Bcl-X (Bcl-x). For test this notion, this example quantify by qRT-PCR the steady-state level of both proapoptotic (CASP2L) and antiapoptotic (CASP2S) forms of caspase 2 mRNAs in both cell lines. Positively correlating with SRSF2 level, CASP2L level in QGY-7703 was 1.5-fold higher than that in SMMC-772 the level of proapoptotic and the antiapoptotic CASP2S was 0.25-fold lower than in SMMC-7721 cells. Taking both measurements into consideration, the ratio of the CASP2L/CASP2S mRNA level in QGY-7703 was 1.94 fold higher than in SMMC-7721 (FIG. 8A).

In light of all the known so far, this ratio is very likely to be most robust indicator to 5-FU resistance of HCC. To determine the 5-FU impact in this system, this example treated both cell lines by 4 μg/mL (a low dose) and 300 μg/mL (a high dose) for one day, respectively. Neither cell lines showed any sickness under microscope even after a high dose of 5-FU treatment. As expected, both RNA and protein of SRSF2 were elevated by a larger margin than E2F1 in both QGY-7703 and SMMC-7721 (FIGS. 8B, C and F). Compatible with the extent of the SRSF2 up-regulation by a low dose of 5-FU, CASP2L RNA (14.62- and 7.38-fold of the untreated level in QGY-7703 and SMMC-7721, respectively) was more drastically up-regulated than CASP2S (1.46- and 1.97-fold of the untreated levels) in both cell lines (FIGS. 8D and E). However, both CASP2S and CASP2L mRNAs were raised by a high-dose 5-FU by a similar extent in both cell lines (FIGS. 8D and E). This example also demonstrates that the intercellular difference (2.94-fold) of the CASP2L/CASP2S mRNA level was preferentially enlarged by 5-FU treatment, particularly for a low dose.

Antagomir Mediated Suppression of miR-193a-3p Inhibited Tumor Growth and Potentiated 5-FU Sensitivity of SMMC-7721 in Nude Mice This example then compared the tumorigenicity of QGY-7703 and SMMC-7721 in nude mice. Whereas subcutaneous injection of $7.5 \times 10^6$ QGY-7703 cells/point produced no visible tumor mass 2 weeks after the injection, $1.25 \times 10^6$ SMCC-7721 cells/injection (⅕ dose of QGY-7703) cells resulted in visible tumor growth (not shown). This indicated that miR-193a-3p expression also involves the HCC tumorigenicity.

SMMC-7721 cells were batch transfected with the miR-193a-3p antagomir and mock antagomir, both SRSF2 and E2F1 protein levels were determined (FIG. 9A) and subcutaneously injected into the right and left flanks of nude mice, respectively. Five mice were subjected to 5-FU or PBS administration on days 18 and 25, respectively. At the same time, the antagomir and mock was respectively intratumorally injected into the corresponding sides of all ten mice (FIG. 9B). The tumor volume of the antagomir-transfected tumor was significantly smaller than the mock antagomir-transfected on day 12 (0.05 vs. 0.2 cm$^3$, P=0.032), on day 25 (0.13 vs. 0.45 cm$^3$, P=0.039) and on day 32 (0.65 vs. 1.03 cm$^3$) (FIG. 9C) and tumor weight on day 32 (0.71 vs. 1.14 g, FIG. 9D). 5-FU administration showed little effect on tumor growth in the mock-transfected SMMC-7721 cells: PBS vs. 5-FU; a) tumor volume: on day 25 (0.46 vs. 0.45 cm$^3$), on day 32 (1.03 vs. 0.89 cm$^3$) (FIG. 9D) and b) tumor weight on day 32 (1.14 vs. 0.82 g, FIG. 9E). However, 5-FU had significant impact on tumor growth in the antagomir treated SMMC-7721 cells: tumor volume on day 32 (0.65 vs. 0.29 cm$^3$, P=0.0427, FIG. 9D); tumor weight on day 32 (0.71 vs. 0.37 g, P=0.0084, FIG. 9E).

The further confirmation of the key role of miR-193a-3p in HCC's 5-FU resistance came from the immunostaining analysis SRSF2, E2F1 and Ki67 (an indicator for cell proliferation) in the tumor session from 5-FU-treated (No. 6) and PBS treated (No. 4) mice. As expected, antagomir treatment raised the SRSF2 level by 20% in tumor xenografts on day 32, regardless of 5-FU administration (FIGS. 9F and G). However, a 20% elevation of E2F1 was evident only in 5-FU/antagomir treated but not in any other cases, suggesting different role and mechanism between of E2F1 and SRSF2 in the miR-193a-3p's dictation of HCC's 5-FU resistance.

Figure 10:
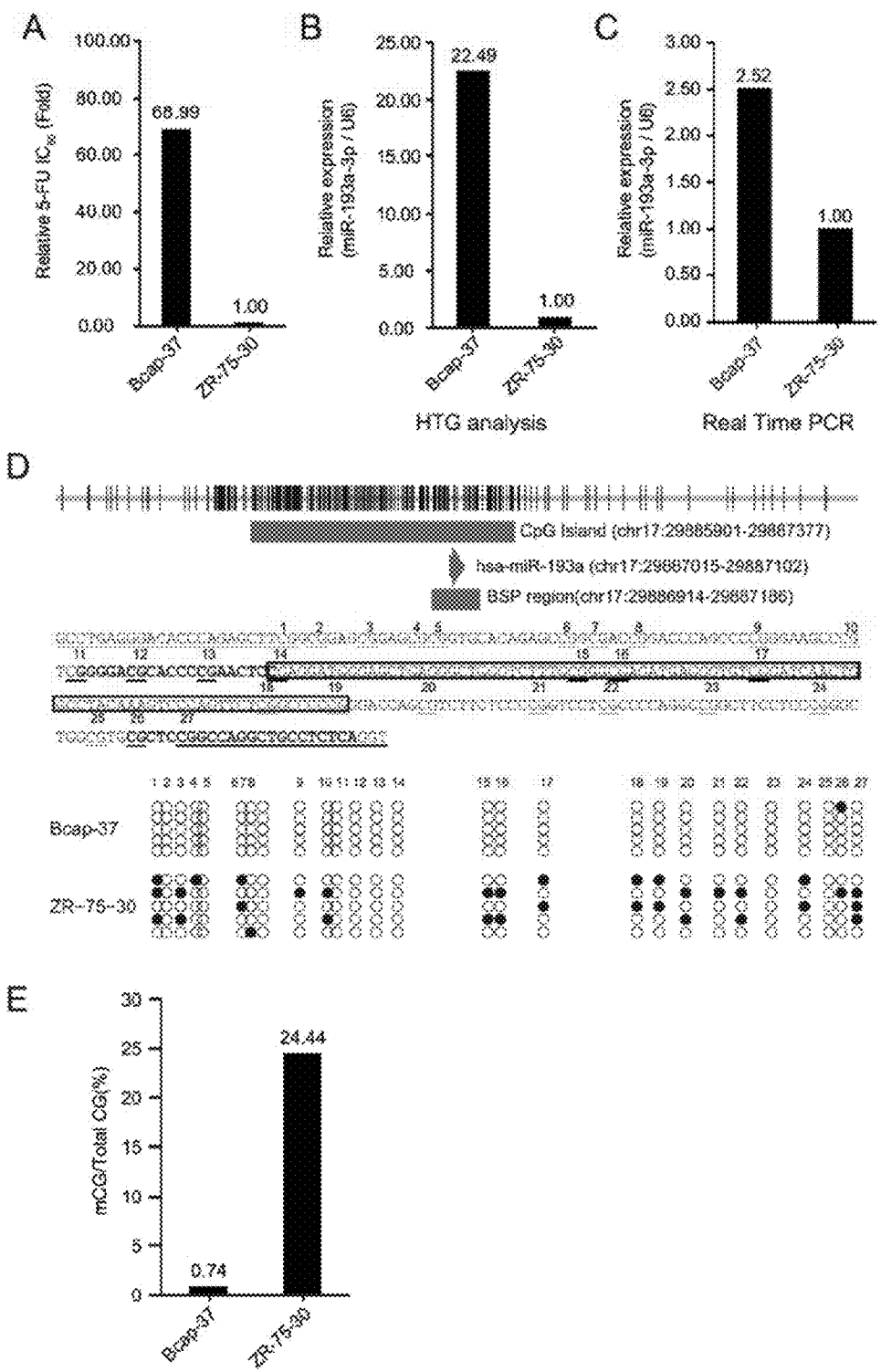
FIG. 10 shows that DNA methylation-regulated miR-193a-3p expression correlates 5-FU sensitivity of ZR-75-30 versus Bcap-37. A. Relative $IC_{50}$ values to 5-FU of f Bcap-37 versus ZR-75-30 (unit: fold). B. Relative miR-193a-3p expression was determined by the quantitative RNAse digestion assay, normalized to the GAPDH gene expression, C. miR-193a-3p expression was determined by qRT-PCR analysis, digitalized with U6 RNA (arbitrarily as 1). D. DNA methylation state of the miR-193a gene in each of seven HCC cell lines was determined by bisulfite sequencing (BSP). The physical map of the CpG island, the gene region, and a 272-bp region containing 27 CpGs analyzed by BSP are indicated. The filled and open circles refer to the methylated and unmethylated CpG, respectively. E. The methylation frequency shown in panel C (unit: mC/Total) is plotted.

The Methylation Regulated miR-193a-3p Expression May Also Contribute to the 5-FU Sensitivity of Breast Cancer Cells This example has also studied whether DNA methylation regulated miR-193a-3p expression plays a role in 5-FU sensitivity of breast cancer cells. Six breast cancer cell lines (MDAMB-231, MDAMB-468, Bcap-37, ZR-75-30, MCF-7 and ZR-75-1) are IC$_{50}$ screened with each of same set of therapeutics. Whereas sharing the similar level of IC$_{50}$ to other therapeutics, Bcap-37 is 69.0 fold more resistant to 5-FU than ZR-75-30 (FIG. 10A) and express more miR-193a-3p by a quantitative RNAse protection assay (Bourzac K. M. et al. (2011) J Biotechnol, 154, 68-75; Pechhold S. et al. (2009) Nat Biotechnol, 27, 1038-1042) (www.htgmolecular.com) (FIG. 10B) and quantitative RT-PCR (FIG. 10C). Indeed, the methylation level of the miR-193a gene was significantly lower in ZR-75-30 than in Bacp-37 (FIGS. 10D and E). Therefore, it is likely that the DNA methylation regulated miR-193a-3p expression also plays a role in the control of the 5-FU resistance in breast cancercell (FIG. 10) and likely in both colon-rectal and gastric cancer, to which treatment 5-FU is often preferred.

The knowledge about cancer has been rapidly expanded for last few decades. However, the ability to control this threatening disease has only been moderately improved, as a patient's survival today is not more than marginally prolonged compared with 40 years ago. Lack of effective measures for early detection and/or accurate stratification of the disease have been largely blamed. Requirement of the companion diagnostics by the USA Food and Drug Administration for approval of newly developed drugs will be soon introduced, highlighting the increasing appreciation of the urgent need for the robust cancer diagnostics. Among all the biologic indicators evaluated, two epigenetic identities, DNA methylation and miRs have garnered a great deal of attention recently, as both promises for the better form of cancer diagnosis Akin to the protein-coding genes, some miR genes are transcriptionally repressed by the hypermethylated states of their promoters, particularly for those collocated with the CpG rich regions in the genome. On the other hand, as other protein-coding genes, expression of DMNT3B, a key regulator of DNA methylation state in mammalian cells, is subjected to regulation by the miR-29 cluster at the level of transcription. It is desirable, hence, to define the molecular details for HCC chemoresistance (5-FU in this study) from both DNA methylation and miR perspectives rather than from each independently.

Figure 2:
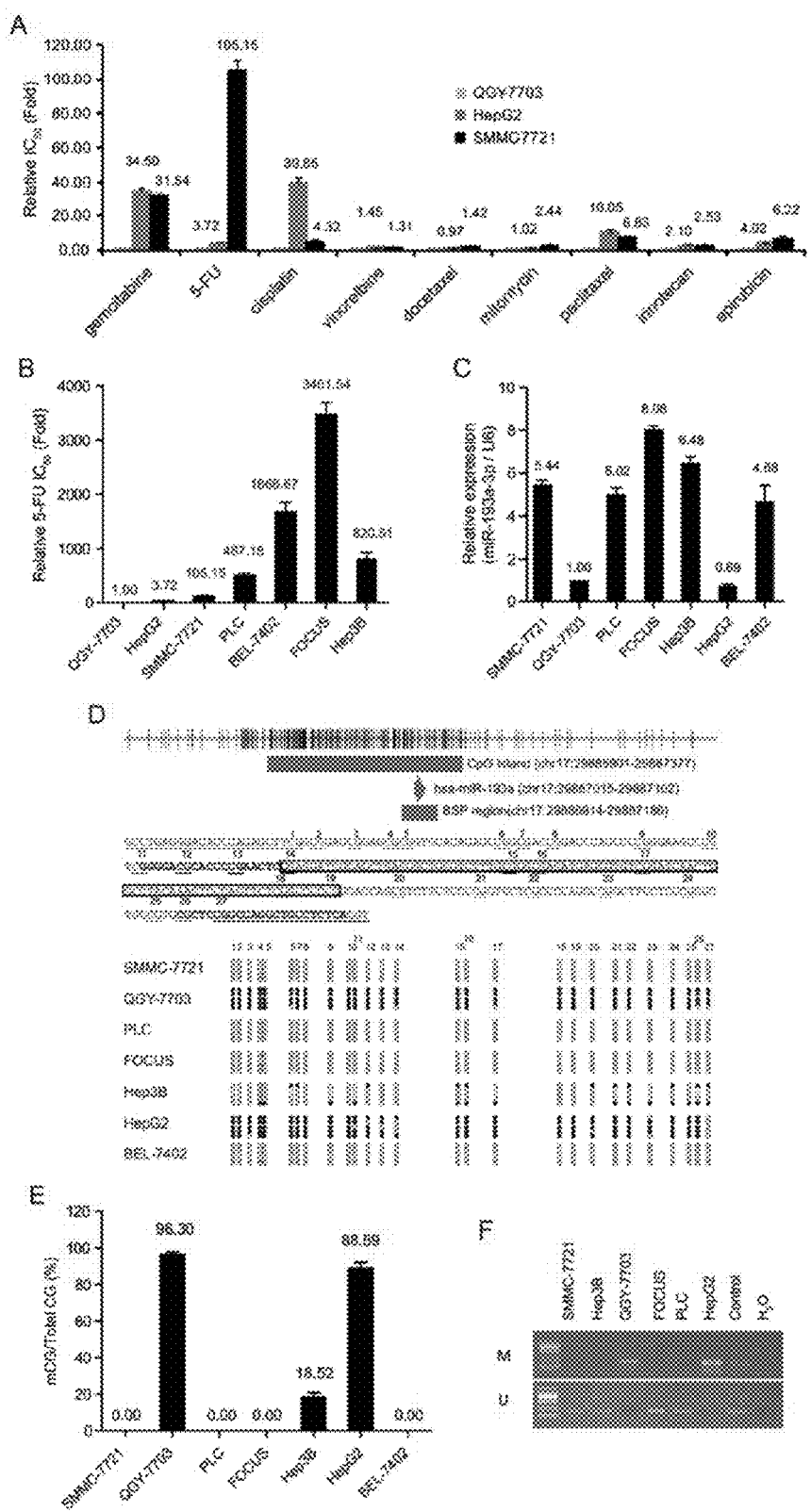
FIG. 2 shows that DNA methylation regulated miR-193a-3p expression correlated with 5-FU sensitivity of HCC cells. A. Relative $IC_{50}$ value of each drug to HepG2 and SMMC-7721 over QGY-7703 was plotted. B. Relative $IC_{50}$ value to 5-FU of each of the six HCC cell lines over QGY-7703 was plotted. C. The relative miR-193a-3p levels in each of seven HCC cell lines were compared by qRT-PCR analysis. D. DNA methylation state of the miR-193a gene in each of seven HCC cell lines was determined by bisulfite sequencing (BSP). The physical map of the CpG island, the gene region, and a 272-bp region containing 27 CpGs analyzed by BSP are indicated. The filled and open circles refer to the methylated and unmethylated CpG, respectively. E. The methylation frequency shown in panel D (unit: $^m$C/Total) is plotted. F. The methylation state of the miR-193a gene in six HCC cell lines was determined by methylation-specific PCR. Control: the unmethylated (U) and methylated (M) control DNA, respectively.
Figure 3:
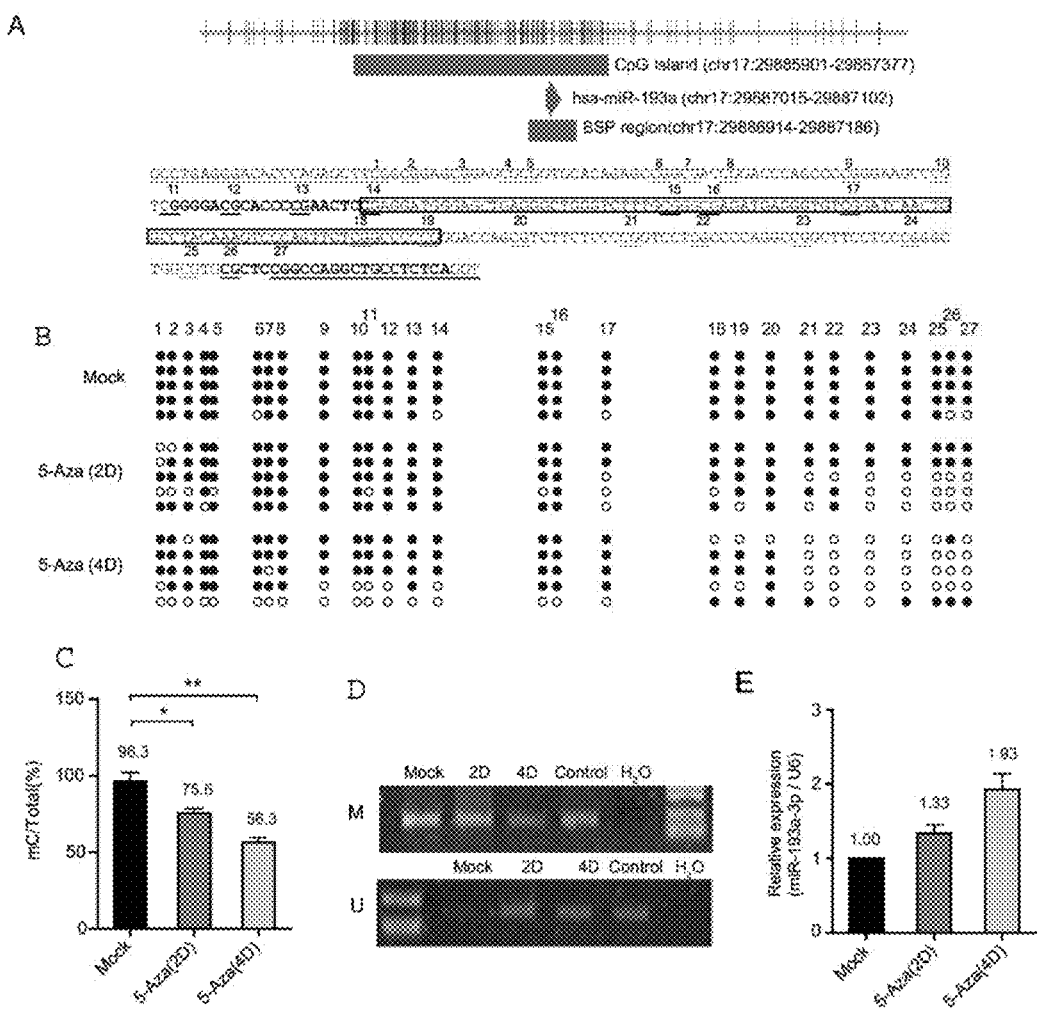
FIG. 3 shows that 5-Aza'-deoxycytidine-mediated demethylation activated miR-193a-3p expression. A. The physical map of the miR-193 gene region for DNA methylation analysis. B. The methylation state of each of 27 CpGs in the mock treated (Mock) and treated for 2 days (2D) and 4 days (4D). C. The methylation frequency in B (unit: mC/Total) is plotted. D. The methylation state of the miR-193a gene determined by methylation-specific PCR is shown. Control: the unmethylated (U) and methylated (M) control DNA, respectively. E. Relative miR-193a-3p level determined by qRT-PCR was plotted. (*P<0.05, **P<0.01).

In this study, this example carried the IC$_{50}$ profiling of eight HCC cell lines to nine common chemotherapeutics and chosen QGY-7703 as a 5-FU-sensitive and SMMC-7721 as a resistant cell lines for the genomic screening at both DNA methylation and miRomic levels for the corresponding difference that are specific to HCC's 5-FU resistance (FIGS. 1A, B and FIG. 2A). Tight association of DNA methylation regulated miR-193a-3p expression with HCC's 5-FU resistance was first suggested by genomic studies (FIG. 1) and then independently confirmed by the qRT-PCR of miR-193a-expression and the DNA methylation analysis (BSP and MSP) in this pair of HCC cell lines (FIG. 1 and FIGS. 2A and 2) and another 5-FU-sensitive cell line, HepG2, and four more resistant cell lines, PLC, BEL-7402, Hep3B, and FOCUS (FIG. 2A-F).

Figure 4:
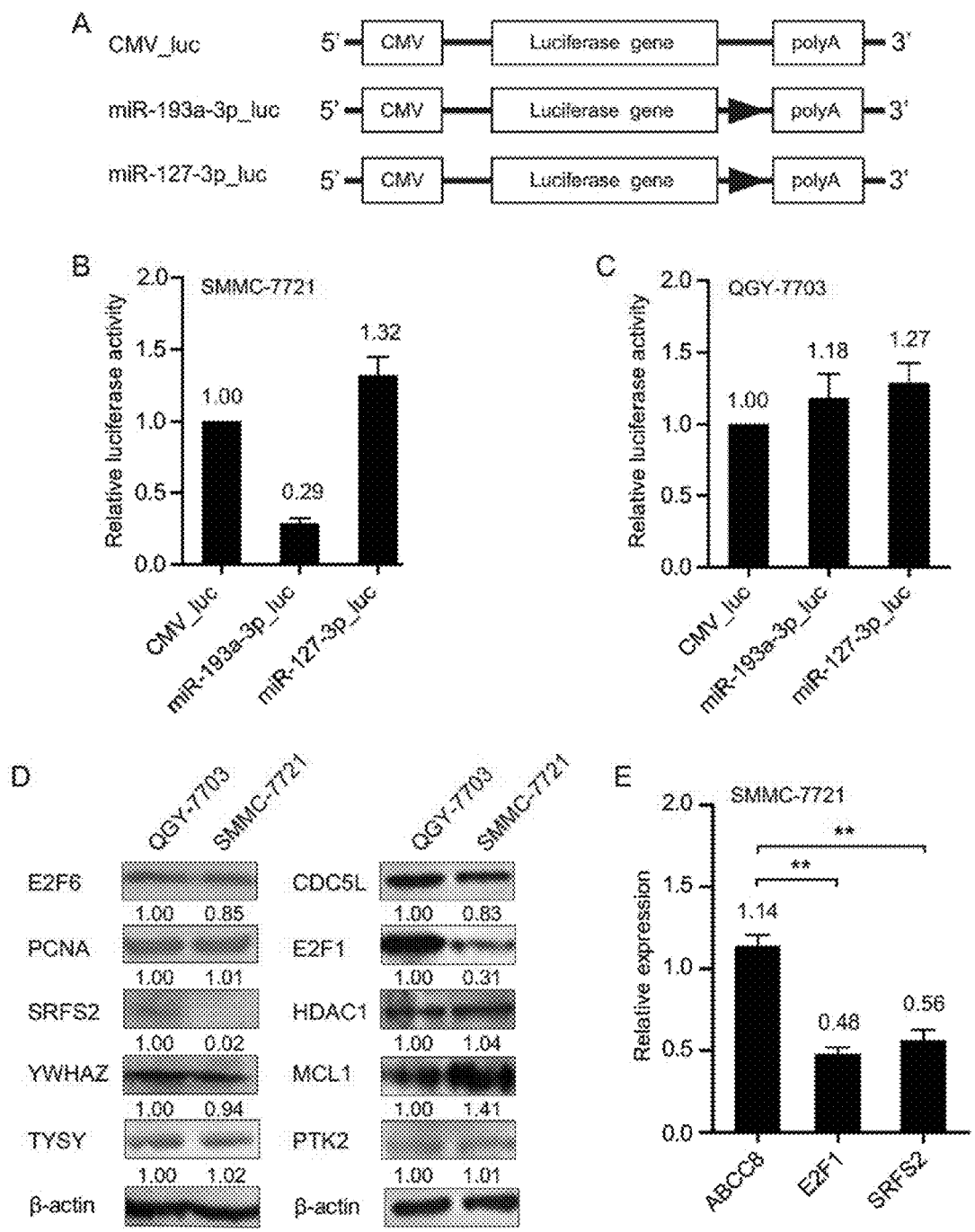
FIG. 4 shows that E2F1 and SRSF2 are bona fide miR-193a-3p targets. A. The constructs used in this study: CMV promoter-driven construct (CMV_luc) and its derivatives (miR-193a-3p-luc and miR-127-luc) with the target sequences (filled triangle) were inserted downstream of the luciferase gene. Each firefly luciferase reporter construct was co-transfected into SMMC-7721 (B) and QGY-7703 (C) with a Renilla luciferase reporter (to control for transfection efficacy). The firefly luciferase activities (mean±SD) were standardized with the Renilla luciferase activities in each transfection and then the relative activities of each over CMV_luc (set arbitrarily as 1) were plotted. D. Protein levels by Western blot analysis were digitalized with β-actin (arbitrarily as 1). E. mRNA levels (2-ΔΔCt) by qRT-PCR analysis were standardized with β-actin (arbitrarily as 1), and the ratios of E2F1 and SRSF2 mRNA to ABCC8 mRNA in SMMC-7721 versus QGY-7703 were calculated and plotted. (**P<0.01).
Figure 7:
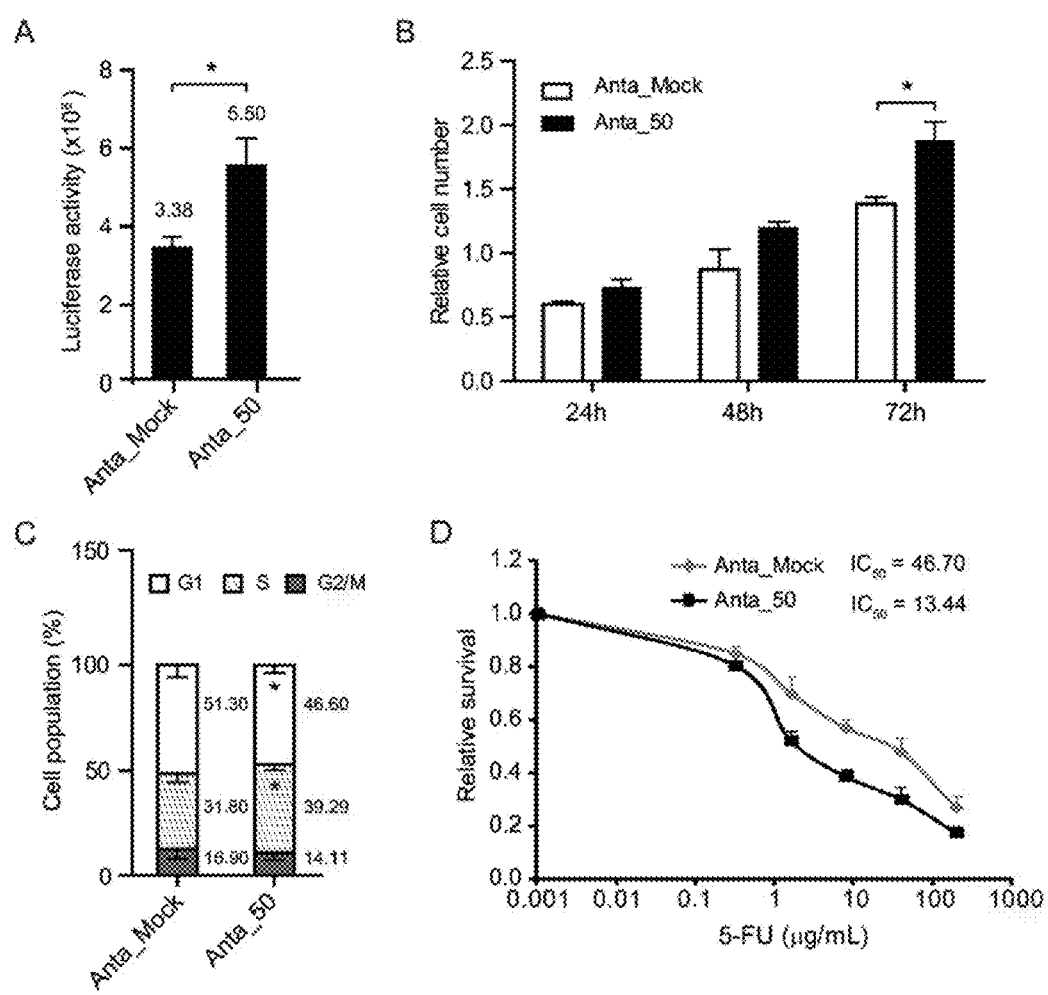
FIG. 7 shows that antagomir-mediated reduction of the miR-193a-3p increased cell proliferation, promoted S phase entry, and enhanced 5-FU sensitivity in SMCC-7721. A. The miR-193a-3p antagomir (50 nM) or an unrelated mimic (mock, 50 nM) was co-transfected with miR-193a-3p-luc into SMMC-7721 and luciferase activity was measured at 24 h after transfection. B. Cell proliferation profile of miR-193a-3p antagomir- and mock-transfected SMMC-7721 was determined by MTT assays. C. Cell cycling profile was analyzed by FACS assays after 48 h transfection. D. The $IC_{50}$ to 5-FU of antagomir- and mock-transfected QGY-7703 was determined, compared and plotted. (*P<0.05, **P<0.01).
Figure 9:
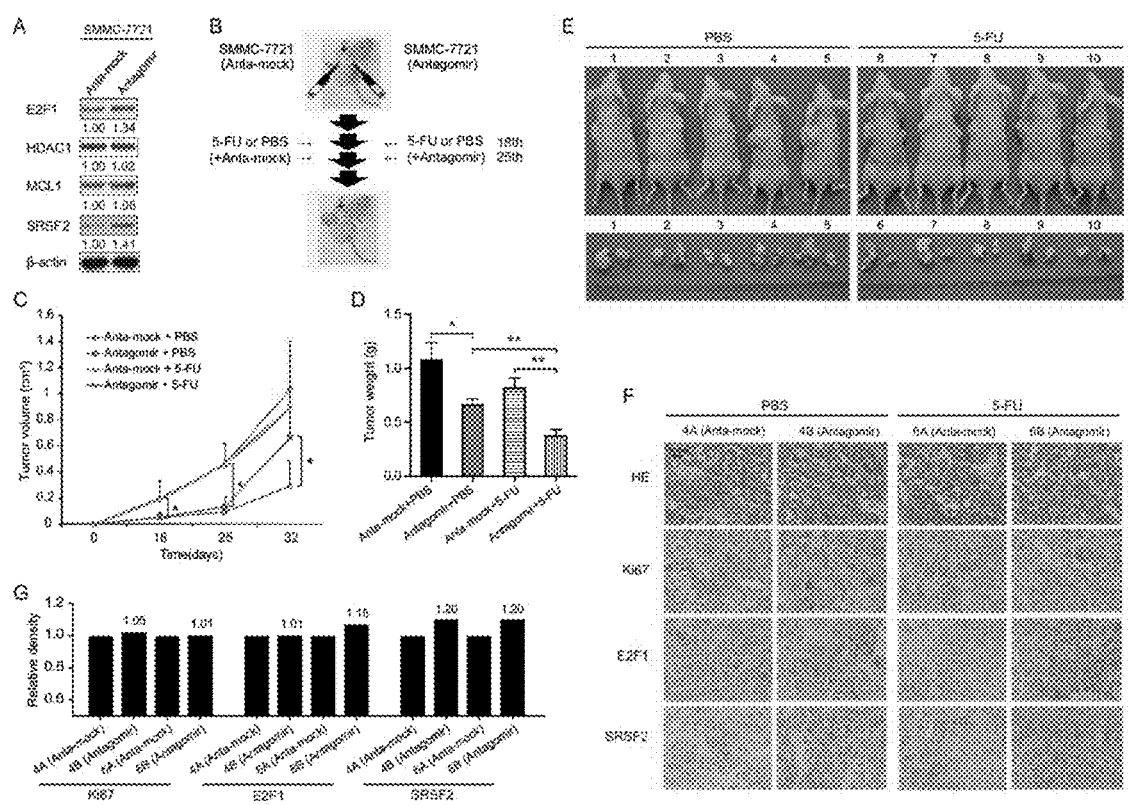
FIG. 9 shows that down-regulation of mR-193a-3p level by antagomir inhibited tumor growth and sensitized SMMC-7721 to 5-FU in nude mice. A. SRSF2, E2F1, HDAC1, and MCL1 proteins were determined by Western blot analysis in the batch of antagomir- and mock-transfected SMMC-7721 cells 48 h after transfection. B. Then the cells (at a dose of $1.25 \times 10^6$ cells/point) were subcutaneously injected into both flanks of nude mice as follows: mock antagomir-transfected on the left and the antagomir-transfected on the right flank, and 5-FU or PBS and antagomir or Mock(Anta-mock) were given on day 12 and 18, and 25, repeated. C. Tumor volume (mean±SD) was measured with a Vernier caliper on days 12, 18, 25, and 32 and compared. D, E. Mice were humanely killed on day 32 and the tumors weigh were measured and photographed (*P<0.05, **P<0.01). F. Levels of Ki67, SRSF2, and E2F1 proteins in tumor tissues of mouse 4 (PBS treatment) and mouse 6 (5-FU treated) were determined by immunostaining G. The level of each protein was quantified as the mean density of the whole area in each slide by using TMAJ software, and then the relative density of mock-versus antagomir-transfected mice was calculated and plotted. (*P<0.05, **P<0.01).

Therefore, the miR-193a-3p centered mechanistic insights detailed by the systematic studies of QGY-7703 and SMMC-7721 are truly specific to 5-FU resistance of HCC. Forced reversion of the miR-193a-3p level in both cell lines have turned around phenotypic features tested: the expression of the target genes (FIGS. 2 and 5), cell proliferation, cell cycling profile, and 5-FU sensitivity (FIG. 4 and FIG. 7). The conclusion was further supported by the observation from the in vivo studies, where repression of the miR-193a-3p level by antagomir technologies repressed tumor growth and sensitized SMMC-7721 cells to 5-FU (FIG. 9). For the key mediators downstream of miR-193a-3p, this example compared both protein and mRNA levels of five bioinformatically predicted miR-193a-3p targets, in both cell lines.

Figure 6:
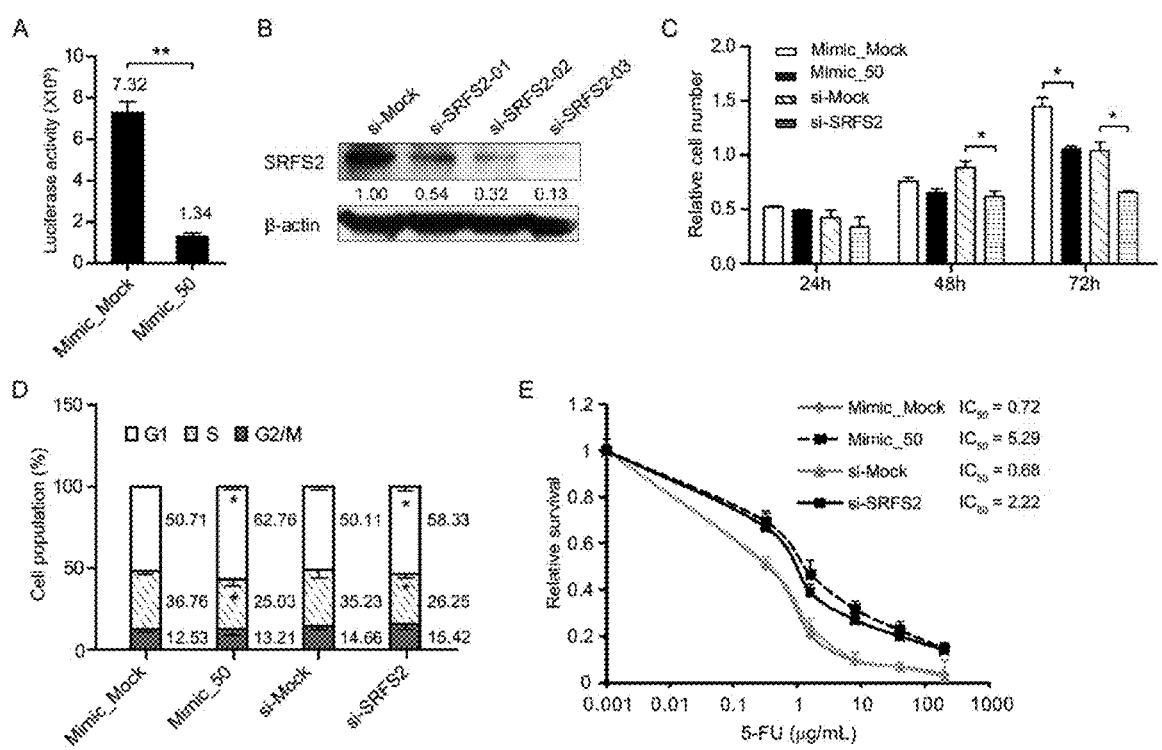
FIG. 6 shows that down-regulation of miR-193a-3p by mimic and of SRSF2 by siRNA transfection resulted in an inhibition of cell proliferation, G1 arrest, and reduced 5-FU sensitivity in QGY-7703. A. miR-193a-3p (50 nM, Mimic_50) or unrelated mimic (mock, 50 nM, Mock-mimic) was co-transfected with miR-193a-3p-luc into QGY-7703 and luciferase activities were measured and plotted. B. SRSF2 levels in the siRNA-01, -02, and -03 or the mock siRNA-transfected QGY-7703 were compared by Western blot analysis at 48 h after transfection. C. Cell numbers were determined by MTT assays at 24, 48 and 72 h after transfection of the miR-193a-3p mimic- and mock-mimic, the SRSF2 siRNA_03 (si_SRSF2), and mock siRNA (Mock_siRNA) into QGY-7703, respectively. D Cycle phase distribution (%) were determined by FACS analysis and plotted. E. $IC_{50}$ to 5-FU values were determined by MTT assays and plotted (*P<0.05, **P<0.01).

SRSF2 and E2F1, but none of others met the expectation: higher in QGY-7703 and lower in SMMC-7721 cells (FIG. 4). Importantly, siRNA mediated repression of SRSF2 phenocopied all the biologic changes in the miR-193a-3p mimic-transfected QGY-7703 (FIG. 6). Up-regulated expression of SRSF2 was also evident in the SMMC-7721-derived tumor xenograft by the antagomir transfection (FIGS. 9F and G). Thus, SRSF2 relays miR-193a-3p's regulation (upstream regulator) via raising the ratio of proapoptotic versus antiapoptotic splicing of the caspase 2, to HCC"s 5-FU resistance (phenotype), to dictating the HCC tumorigenicity and 5-FU resistance (FIG. 11).

Deregulation of the E2F transcription factors is a hallmark of cancer, often indicative of a poor prognosis. E2F1 controls transcription of the multiple genes, each directly or indirectly involves in the regulation of $G_1$-S phase entry (cell proliferation) or apoptosis of cells. E2F1 activation triggered by DNA damage is often reflects by the favorable changes in its chemical modification state and its interaction state with the retinoblastoma protein. As a E2F1 target, SRSF2 transcription is also up-regulated in the stressed cell, and consequently the ratio of the proapoptotic to the antiapoptotic splicing form of the apoptotic genes rises. This example showed for the first time that both SRSF2 and E2F1 are bona fide targets of miR-193a-3p (FIG. 4).

Figure 8:
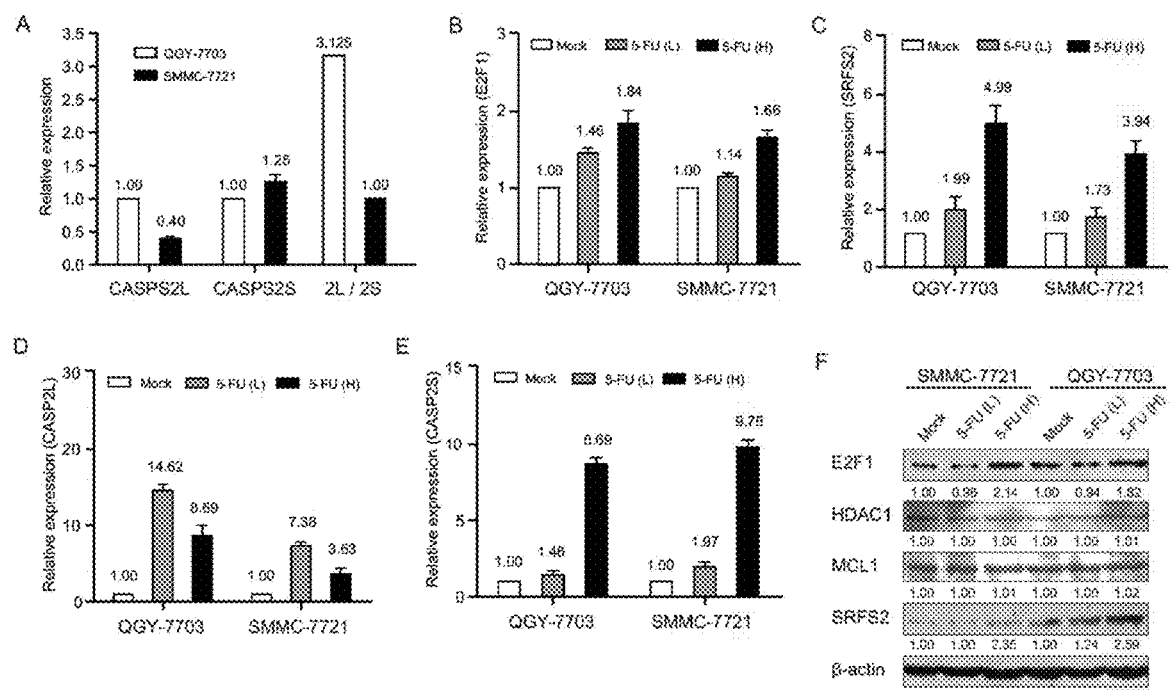
FIG. 8 shows that 5-FU triggered the expression of E2F1, SRSF2 and the proapoptotic splice form of caspase 2 in both cell lines. A. The mRNA levels of both CASP2L (proapoptotic slicing form) and CASP2S (antiapoptotic form) of caspase 2 in both QGY-7703 (open column) and SMMC-7721 (filled column) were quantified by qRT-PCR and compared. The effects of 5-FU on the mRNA levels of E2F21 (B), SRSF2 (C), CASP2L(D), and CASP2S (E) in mock- and 5-FU-treated cells were assessed at 24 h after treatment with a low dose, 4 μg/mL 5-FU(L), or a high dose, 300 μg/mL 5-FU(H), then with mock control (set arbitrarily as 1). F. The protein levels of E2F1, SRSF2, HDAC1, MCL1, and β-actin in the mock- and 5-FU-treated cells were examined by Western blot.

Therefore, the miR-193a-3p depended SRSF2 expression consists of a direct and an indirect components. The E2F1 mediated component, well explains why the SRSF2 always responds more profoundly than E2F1 to the change of miR193a-3p level in cell (FIG. 4-9). The genotoxic insults may also trigger both phosphorylation and acetylation and changes SRSF2 activity, representing a E2F1 independent pathway for SRSF2 activation in the DNA damaged cells. SRSF2 is a key member of a serine/arginine-rich protein family that regulates constitutive and alternative pre-mRNA splicing for extensive diversities in gene expression that are evident across tissues, developmental stages, and diseases. Multiple forms of protein are often generated from a single primary transcript, having different and even opposite functions. The eminent examples in cancer field are proapoptotic versus antiapoptotic isoforms of the caspase genes as well as pro-oncogenic versus anti-oncogenic isoforms of BRCA1 and CD44. The aberrant RNA splicing in cancer has been attributed to the mutations in cis-motifs and to both genetic defects and aberrant expression of the protein components of the mRNA splicing machinery. The stressed cells often have a high level of both RNA splicing activity, and the proapoptotic form of the apoptotic genes. Consistent with this, the ratio of the proapoptotic/antiapoptotic forms of the caspase 2 transcript in 5-FU-sensitive QGY-7703 is higher than that in resistant SMMC-7721 (FIG. 8) and rise rose in the 5-FU treated HCC cells (FIG. 8). Therefore, in comparison with other events, this ratio is a better indicator for both 5-FU resistance and tumorigenicity of HCC.

Several molecular events have been implicated in the 5-FU resistance of cancer cells. For instance, the association of the overexpressed astrocyte elevated gene-1 (AEG-1) with 5-FU resistance of HCC cells was ascribed to the ability of AEG-1 to activate the transcription the genes that catabolize 5-FU. Other indicators for cancer cell's resistance to 5-FU include dysregulated Ep-CAM, Hsp27 and Hsp40 proteins. miR-21 represses hMSH2 expression, which was reported overexpressed in colorectal cancers that are refractory to 5-FU therapy. Taken together, this example showed for the first time that miR-193a-3p regulates HCC's 5-FU resistance and its transcription is repressed by the hypermethylated promoter state. Both SRSF2 and E2F1 are true targets of miR-193a-3p, SRSF2 is the key mediator to relay the miR-193a-3p's regulation to HCC's resistance to 5-FU. Both tumorigenicity and 5-FU resistance of HCC cells are directly associated with SRSF2's ability to elevate the ratio of the proapoptotic/antiapoptotic forms of the caspase 2 transcript. Finally, the observation detailed in this report suggests a list of novel candidates as prognostic indicators for rational 5-FU therapy of HCC: DNA methylation state or the levels of miR-193a-3p, SRSF2, E2F1, and the proapoptotic form of caspase 2.

The disclosure illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosure embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A method for selecting a breast cancer patient for a therapy comprising the administration of 5-FU, the method comprising:

measuring, in a breast tumor sample isolated from the patient, the methylation status of one or more CpG sites associated with the miR-193a gene, wherein the methylation of the one or more CpG site decreases the expression level of the miR-193a-3p RNA, and selecting the patient for the therapy when the methylation of the one or more CpG sites is present in the tumor sample.

2. The method of claim 1, wherein the tumor sample comprises a tumor cell.

3. The method of claim 2, wherein the measurement is performed with a primer, a probe, or an antibody.

4. The method of claim 1, wherein the tumor sample comprises a tumor DNA.

5. The method of claim 1, wherein the measurement is performed before the patient receives the therapy.

6. A method for selecting a breast cancer patient for a therapy comprising the administration of 5-FU, the method comprising measuring, in a breast tumor sample isolated from the patient, the methylation status of one or more CpG sites associated with the miR-193a gene, wherein the methylation of the one or more CpG site decreases the expression level of the miR-193a-3p RNA, and selecting the patient for the therapy when the methylation of the one or more CpG sites is present in the tumor sample, and wherein the measurement is performed with a primer, a probe, or an antibody.

7. A method for treating a breast cancer patient, comprising administering to the patient an effective amount of a therapy comprising 5-FU, wherein the patient is selected for the therapy based on the presence, in a breast tumor sample isolated from the patient, of methylation of one or more CpG sites associated with the miR-193a gene that decreases the expression level of the miR-193a-3p RNA.

8. The method of claim 7, further comprising, prior to the administration, measuring, in a breast tumor sample isolated from the patient, the methylation status of the one or more CpG sites.

* * * * *

SEQUENCE LISTING

```
<160> NUMBER OF SEQ ID NOS: 23

<210> SEQ ID NO 1
<211> LENGTH: 22
<212> TYPE: RNA
```

<213> ORGANISM: Homo sapiens

<400> SEQUENCE: 1
aacuggccua caaaguccca gu                                             22

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aatttgggtc tttgcgggcg agatgat                                        27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acccagaaac gcccgctcta ctagatc                                        27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aattctgaag ctcagagggc tctgatt                                        27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gacttcgagt ctcccgagac taagatc                                        27

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcacccacac tgtgcccatc tacga                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 7
cagcggaacc gctcattgcc aatgg                                              25

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cacagatccc agccagtctc ta                                                 22

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagaagtccc gcacatg                                                       17

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccactcagag ctatgagcta cg                                                 22

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
actccttggt gtagcgatcc                                                    20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctgccgtgg agatgaga                                                      18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 13
tcggcaactt ttctttaccg                                               20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cttgggcacc tccttctgt                                                19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtgaccgaa tcccaccatc                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagggcaatt agcagcttgg                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggggacgtat ttcgaatttc                                               20

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taaaaaacaa cctaaccgaa acg                                           23

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
```

```
gggatgtat tttgaatttt ga                                              22
```

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
acacacacca acccaaaaa                                                 19
```

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
gtttgaggga tatttagagt tt                                             22
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
acctaaaaaa caacctaacc                                                20
```

<210> SEQ ID NO 23
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
gcctgaggga cacccagagc ttcggcggag cggagcgcgg tgcacagagc cggcgaccgg     60
acccagcccc gggaagcccg tcggggacgc accccgaact ccgaggatgg gagctgaggg    120
ctgggtcttt gcgggcgaga tgagggtgtc ggatcaactg gcctacaaag tcccagttct    180 cggccccecgg gaccagcgtc ttctccccgg tcctcgcccc aggccggctt cctcccgggc    240
tggcgtgcgc tccggccagg ctgcctctca ggt                                 273
```